United States Patent [19]
Christensen, IV et al.

[11] Patent Number: 5,861,421
[45] Date of Patent: Jan. 19, 1999

[54] 4,4-(DISUBSTITUTED) CYCLOHEXAN-1-ONE MONOMERS AND RELATED COMPOUNDS

[75] Inventors: Siegfried B. Christensen, IV, Philadelphia; Joseph M. Karpinski; M. Dominic Ryan, both of Pottstown, all of Pa.; Paul E. Bender, Cherry Hill, N.J.

[73] Assignee: SmithKline Beecham Corporation, Philadelphia, Pa.

[21] Appl. No.: 860,404

[22] PCT Filed: Dec. 21, 1995

[86] PCT No.: PCT/US95/16858

§ 371 Date: Jun. 23, 1997

§ 102(e) Date: Jun. 23, 1997

[87] PCT Pub. No.: WO96/19995

PCT Pub. Date: Jul. 4, 1996

[51] Int. Cl.$^6$ .......................... C07D 405/10; A61K 31/44
[52] U.S. Cl. .......................... 514/338; 544/318; 544/332; 546/226; 546/270; 546/340; 549/61; 549/71; 549/341; 549/342; 558/405; 548/131; 548/136; 548/143; 548/341.5; 560/53; 564/219; 564/360; 568/330; 562/463

[58] Field of Search ...................... 548/131, 136, 548/143, 341.5; 544/318, 332; 546/226, 270, 340; 549/61, 71, 341, 342; 558/405; 560/53; 564/219, 360; 568/330; 562/463; 514/338

[56] References Cited

PUBLICATIONS

Chemical Abstracts vol. 120, No. 19 9 May 94 Abstract No. 244187D *Preparation of arylcyclohexenes as drugs.*

*Primary Examiner*—Robert Gerstl
*Attorney, Agent, or Firm*—James M Kanagy; Stephen Venetianer

[57] ABSTRACT

This invention relates to derivatives of 4,4-(disubstituted) cyclohexan-1-ones and related compounds which are useful for treating allergic and inflammatory diseases.

10 Claims, No Drawings

4,4-(DISUBSTITUTED) CYCLOHEXAN-1-ONE MONOMERS AND RELATED COMPOUNDS

FIELD OF INVENTION

The present invention relates to novel 4,4-(disubstituted) cyclohexan-1-ones and related compounds, pharmaceutical compositions containing these compounds, and their use in treating allergic and inflammatory diseases and for inhibiting the production of Tumor Necrosis Factor (TNF).

BACKGROUND OF THE INVENTION

Bronchial asthma is a complex, multifactorial disease characterized by reversible narrowing of the airway and hyperreactivity of the respiratory tract to external stimuli.

Identification of novel therapeutic agents for asthma is made difficult by the fact that multiple mediators are responsible for the development of the disease. Thus, it seems unlikely that eliminating the effects of a single mediator will have a substantial effect on all three components of chronic asthma. An alternative to the "mediator approach" is to regulate the activity of the cells responsible for the pathophysiology of the disease.

One such way is by elevating levels of cAMP (adenosine cyclic 3',5'-monophosphate). Cyclic AMP has been shown to be a second messenger mediating the biologic responses to a wide range of hormones, neurotransmitters and drugs; [Krebs Endocrinology Proceedings of the 4th International Congress Excerpta Medica, 17–29, 1973]. When the appropriate agonist binds to specific cell surface receptors, adenylate cyclase is activated, which converts $Mg^{+2}$-ATP to cAMP at an accelerated rate.

Cyclic AMP modulates the activity of most, if not all, of the cells that contribute to the pathophysiology of extrinsic (allergic) asthma. As such, an elevation of cAMP would produce beneficial effects including: 1) airway smooth muscle relaxation, 2) inhibition of mast cell mediator release, 3) suppression of neutrophil degranulation, 4) inhibition of basophil degranulation, and 5) inhibition of monocyte and macrophage activation. Hence, compounds that activate adenylate cyclase or inhibit phosphodiesterase should be effective in suppressing the inappropriate activation of airway smooth muscle and a wide variety of inflammatory cells. The principal cellular mechanism for the inactivation of cAMP is hydrolysis of the 3'-phosphodiester bond by one or more of a family of isozymes referred to as cyclic nucleotide phosphodiesterases (PDEs).

It has now been shown that a distinct cyclic nucleotide phosphodiesterase (PDE) isozyme, PDE IV, is responsible for cAMP breakdown in airway smooth muscle and inflammatory cells. [Torphy, "Phosphodiesterase Isozymes: Potential Targets for Novel Anti-asthmatic Agents" in New Drugs for Asthma, Barnes, ed. IBC Technical Services Ltd., 1989]. Research indicates that inhibition of this enzyme not only produces airway smooth muscle relaxation, but also suppresses degranulation of mast cells, basophils and neutrophils along with inhibiting the activation of monocytes and neutrophils. Moreover, the beneficial effects of PDE IV inhibitors are markedly potentiated when adenylate cyclase activity of target cells is elevated by appropriate hormones or autocoids, as would be the case in vivo. Thus PDE IV inhibitors would be effective in the asthmatic lung, where levels of prostaglandin $E_2$ and prostacyclin (activators of adenylate cyclase) are elevated. Such compounds would offer a unique approach toward the pharmacotherapy of bronchial asthma and possess significant therapeutic advantages over agents currently on the market.

The compounds of this invention also inhibit the production of Tumor Necrosis Factor (TNF), a serum glycoprotein. Excessive or unregulated TNF production has been implicated in mediating or exacerbating a number of diseases including rheumatoid artritis, rheumatoid spondylitis, osteoarthritis, gouty arthritis and other arritic conditions; sepsis, septic shock, endotoxic shock, gram negative sepsis, toxic shock syndrome, adult respiratory distress syndrome, cerebral malaria, chronic pulmonary inflammatory disease, silicosis, pulmonary sarcoidosis, bone resorption diseases, reperfusion injury, graft vs. host reaction, allograft rejections, fever and myalgias due to infection, such as influenza, cachexia secondary to infection or malignancy, cachexia secondary to human acquired immune deficiency syndrome (AIDS), AIDS, ARC (AIDS related complex), keloid formation, scar tissue formation, Crohn's disease, ulcerative colitis, or pyresis, in addition to a number of autoimmune diseases, such as multiple sclerosis, autoimmune diabetes and systemic lupus erythematosis.

AIDS results from the infection of T lymphocytes with Human Immunodeficiency Virus (HIV). At least three types or strains of HIV have been identified, i.e., HIV-1, HIV-2 and HIV-3. As a consequence of HIV infection, T-cell-mediated immunity is impaired and infected individuals manifest severe opportunistic infections and/or unusual neoplasms. HIV entry into the T lymphocyte requires T lymphocyte activation. Viruses such as HIV-1 or HIV-2 infect T lymphocytes after T cell activation and such virus protein expression and/or replication is mediated or maintained by such T cell activation. Once an activated T lymphocyte is infected with HIV, the T lymphocyte must continue to be maintained in an activated state to permit HIV gene expression and/or HIV replication.

Cytokines, specifically TNF, are implicated in activated T-cell-mediated HIV protein expression and/or virus replication by playing a role in maintaining T lymphocyte activation. Therefore, interference with cytokine activity such as by inhibition of cytokine production, notably TNF, in an HIV-infected individual aids in limiting the maintenance of T cell activation, thereby reducing the progression of HIV infectivity to previously uninfected cells which results in a slowing or elimination of the progression of immune dysfunction caused by HIV infection. Monocytes, macrophages, and related cells, such as kupffer and glial cells, have also been implicated in maintenance of the HIV infection. These cells, like T cells, are targets for viral replication and the level of viral replication is dependent upon the activation state of the cells. [See Rosenberg et al., The Immunopathogenesis of HIV Infection, Advances in Immunology, Vol. 57, 1989]. Monokines, such as TNF, have been shown to activate HIV replication in monocytes and/or macrophages [See Poli et al., Proc. Natl. Acad. Sci., 87:782–784, 1990], therefore, inhibition of monokine production or activity aids in limiting HIV progression as stated above for T cells.

TNF has also been implicated in various roles with other viral infections, such as the cytomegalovirus (CMV), influenza virus, adenovirus, and the herpes virus for similar reasons as those noted.

TNF is also associated with yeast and fungal infections. Specifically *Candida albicans* has been shown to induce TNF production in vitro in human monocytes and natural killer cells. [See Riipi et al., Infection and Immunity, 58(9):2750–54, 1990; and Jafari et al., Journal of Infectious Diseases, 164:389–95, 1991. See also Wasan et al., Antimicrobial Agents and Chemotherapy, 35,(10):2046–48, 1991; and Luke et al., Journal of Infectious Diseases, 162:211–214,1990].

The ability to control the adverse effects of TNF is furthered by the use of the compounds which inhibit TNF in mammals who are in need of such use. There remains a need for compounds which are useful in treating TNF-mediated disease states which are exacerbated or caused by the excessive and/or unregulated production of TNF.

SUMMARY OF THE INVENTION

The novel compounds of this invention are represented by Formula (I):

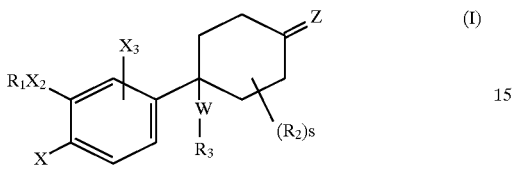

(I)

wherein:
$R_1$ is —$(CR_4R_5)_nC(O)O(CR_4R_5)_mR_6$, —$(CR_4R_5)_nC(O)NR_4(CR_4R_5)_mR_6$, —$(CR_4R_5)_nO(CR_4R_5)_mR_6$, or —$(CR_4R_5)_rR_6$ wherein the alkyl moieties may be unsubstituted or substituted with one or more fluorines;

m is 0 to 2;
n is 0 to 4;
r is 0 to 6;
$R_4$ and $R_5$ are independently hydrogen or $C_{1-2}$ alkyl;
$R_6$ is hydrogen, methyl, hydroxyl, aryl, halo substituted aryl aryloxy$C_{1-3}$ alkyl, halo substituted aryloxy$C_{1-3}$ alkyl, indanyl indenyl, $C_{7-11}$ polycycloalkyl, tetrahydrofuranyl, furanyl, tetrahydropyranyl pyranyl, tetrahydrothienyl, thienyl, tetrahydrothiopyranyl, thiopyranyl, $C_{3-6}$ cycloalkyl, or a $C_{4-6}$ cycloalkyl containing one or two unsaturated bonds, wherein the cycloalkyl or heterocyclic moiety may be unsubstituted or substituted by 1 to 3 methyl groups, one ethyl group or an hydroxyl group;

provided that:
a) when $R_6$ is hydroxyl, then m is 2; or
b) when $R_6$ is hydroxyl, then r is 2 to 6; or
c) when $R_6$ is 2-tetrahydropyranyl, 2-tetrahydrothiopyranyl, 2-tetrahydrofuranyl, or 2-tetrahydrothienyl, then m is 1 or 2; or
d) when $R_6$ is 2-tetrahydropyranyl, 2-tetrahydrothiopyranyl, 2-tetrahydrofuranyl, or 2-tetrahydrothienyl, then r is 1 to 6;
e) when n is 1 and m is 0, then $R_6$ is other than H in —$(CR_4R_5)_nO(CR_4R_5)_mR_6$;

X is $YR_2$, fluorine, $NR_4R_5$, or formyl amine;
Y is O or $S(O)_{m'}$;
m' is 0, 1, or 2;
$X_2$ is O or $NR_8$;
$X_3$ is hydrogen or X;
$R_2$ is —$CH_3$ or —$CH_2CH_3$ unsubstituted or substituted by 1 or more fluorines;
s is 0 to 4;
$R_3$ is $COOR_{14}$, $C(O)NR_4R_{14}$ or $R_7$;
W is alkyl of 2 to 6 carbons, alkenyl of 2 to 6 carbon atoms or alkynyl of 2 to 6 carbon atoms;
Z is O, $NR_7$, $NCR_4R_5C_{2-6}$ alkenyl, $NOR_{14}$, $NOR_{15}$, $NOCR_4R_5C_{2-6}$ alkenyl, $NNR_4R_{14}$, $NNR_4R_{15}$, NCN, $NNR_8C(O)NR_8R_{14}$, $NNR_8C(S)NR_8R_{14}$, or =Z is 2-(1,3-dithiane), 2-(1,3-dithiolane), dimethylthio ketal, diethylthio ketal, 2-(1,3-dioxolane), 2(1,3-dioxane), 2-(1,3-oxathiolane), dimethyl ketal or diethyl ketal;

$R_7$ is —$(CR_4R_5)_qR_{12}$ or $C_{1-6}$ alkyl wherein the $R_{12}$ or $C_{1-6}$ alkyl group is unsubstituted or substituted one or more times by methyl or ethyl unsubstituted or substituted by 1–3 fluorines, —F, —Br, —Cl, —$NO_2$, —$NR_{10}R_{11}$, —$C(O)R_8$, —$CO_2R_8$, —$O(CH_2)_{2-4}OR_8$, —$O(CH_2)_qR_8$, —CN, —$C(O)NR_{10}R_{11}$, —$O(CH_2)_qC(O)NR_{10}R_{11}$, —$O(CH_2)_qC(O)R_9$, —$NR_{10}C(O)NR_{10}R_{11}$, —$NR_{10}C(O)R_{11}$, —$NR_{10}C(O)OR_9$, —$NR_{10}C(O)R_{13}$, —$C(NR_{10})NR_{10}R_{11}$, —$C(NCN)NR_{10}R_{11}$, —$C(NCN)SR_9$, —$NR_{10}C(NCN)SR_9$, —$NR_{10}C(NCN)NR_{10}R_{11}$, —$NR_{10}S(O)_2R_9$, —$S(O)_mR_9$, —$NR_{10}C(O)C(O)NR_{10}R_{11}$, —$NR_{10}C(O)C(O)R_{10}$, or $R_{13}$;

q is 0, 1, or 2;
$R_{12}$ is $R_{13}$, $C_3$–$C_7$ cycloalkyl, (2-, 3- or 4-pyridyl), pyrimidyl, pyrazolyl, (1- or 2-imidazolyl), pyrrolyl, piperazinyl, piperidinyl, morpholinyl, furanyl, (2- or 3-thienyl), quinolinyl, naphthyl, or phenyl;
$R_8$ is hydrogen or $R_9$;
$R_9$ is $C_{1-4}$ alkyl unsubstituted or substituted by one to three fluorines;
$R_{10}$ is $OR_8$ or $R_{11}$;
$R_{11}$ is hydrogen, or $C_{1-4}$ alkyl unsubstituted or substituted by one to three fluorines; or when $R_{10}$ and $R_{11}$ are as $NR_{10}R_{11}$ they may together with the nitrogen form a 5 to 7 membered ring comprised only of carbon atoms or carbon atoms and at least one heteroatom selected from O, N, or S;
$R_{13}$ is a substituted or unsubstituted heteroaryl group selected from the group consisting of oxazolidinyl, oxazolyl, thiazolyl, pyrazolyl, triazolyl, tetrazolyl, imidazolyl, imidazolidinyl, thiazolidinyl, isoxazolyl, oxadiazolyl, and thiadiazolyl, and where $R_{13}$ is substituted on $R_{12}$ or $R_{13}$ the rings are connected through a carbon atom and each second $R_{13}$ ring may be unsubstituted or substituted by one or two $C_{1-2}$ alkyl groups unsubstituted or substituted on the methyl with 1 to 3 fluoro atoms;
$R_{14}$ is hydrogen or $R_7$; or when $R_8$ and $R_{14}$ are as $NR_8R_{14}$ they may together with the nitrogen form a 5 to 7 membered ring comprised only of carbon atoms or carbon atoms and at least one heteroatom selected from O, N, or S; provided that:

(f) $R_7$ is not $C_{1-4}$ alkyl unsubstituted or substituted by one to three fluorines; or
or the pharmaceutically acceptable salts thereof.

Another set of compounds of this invention are represented by Formula (II)

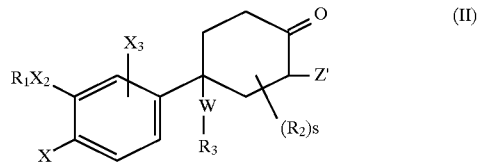

(II)

wherein:
$R_1$ is —$(CR_4R_5)_nC(O)O(CR_4R_5)_mR_6$, —$(CR_4R_5)_nC(O)NR_4(CR_4R_5)_mR_6$, —$(CR_4R_5)_nO(CR_4R_5)_mR_6$, or —$(CR_4R_5)_rR_6$ wherein the alkyl moieties may be unsubstituted or substituted with one or more fluorines;

m is 0 to 2;

n is 0 to 4;

r is 0 to 6;

$R_4$ and $R_5$ are independently selected hydrogen or $C_{1-2}$ alkyl;

$R_6$ is hydrogen, methyl, hydroxyl, aryl, halo substituted aryl, aryloxy$C_{1-3}$ alkyl, halo substituted aryloxy$C_{1-3}$ alkyl, indanyl, indenyl, $C_{7-11}$ polycycloalkyl, tetrahydrofaranyl, faranyl, tetrahydropyranyl pyranyl, tetrahydrothienyl thienyl, tetrahydrothiopyranyl, thiopyranyl, $C_{3-6}$ cycloalkyl, or a $C_{4-6}$ cycloalkyl containing one or two unsaturated bonds, wherein the cycloalkyl and heterocyclic moieties is unsubstituted or substituted by 1 to 3 methyl groups, an ethyl group, or an hydroxyl group;

provided that:
a) when $R_6$ is hydroxyl, then m is 2; or
b) when $R_6$ is hydroxyl, then r is 2 to 6; or
c) when $R_6$ is 2-tetrahydropyranyl, 2-tetrahydrothiopyranyl, 2-tetrahydrofuranyl, or 2-tetrahydrothienyl, then m is 1 or 2; or
d) when $R_6$ is 2-tetrahydropyranyl, 2-tetrahydrothiopyranyl, 2-tetrahydrofuranyl, or 2-tetrahydrothienyl, then r is 1 to 6;
e) when n is 1 and m is 0, then $R_6$ is other than H in —$(CR_4R_5)_nO(CR_4R_5)_mR_6$;

X is $YR_2$, fluorine, $NR_4R_5$, or formyl amine;

Y is O or $S(O)_{m'}$;

m' is 0, 1, or 2;

$X_2$ is O or $NR_8$;

$X_3$ is hydrogen or X;

$R_2$ is independently selected from —$CH_3$ or —$CH_2CH_3$ unsubstituted or substituted by 1 or more fluorines;

s is 0 to 4;

$R_3$ is $COOR_{14}$, $C(O)NR_4R_{14}$ or $R_7$;

W is alkyl of 2 to 6 carbons, alkenyl of 2 to 6 carbon atoms or alkynyl of 2 to 6 carbon atoms;

Z' is $C(Y')R_{14}$, $C(O)OR_{14}$, $C(Y')NR_{10}R_{14}$, $C(NR_{10})NR_{10}R_{14}$, CN, $C(NOR_8)R_{14}$, $C(O)NR_8NR_8C(O)R_8$, $C(O)NR_8NR_{10}R_{14}$, $C(NOR_{14})R_8$, $C(NR_8)NR_{10}R_{14}$, $C(NR_{14})NR_8R_8$ $C(NCN)NR_{10}R_{14}$, $C(NCN)SR_9$, (2-, 4- or 5-imidazolyl), (3-, 4- or 5-pyrazolyl), (4- or 5-triazolyl[1,2,3]), (3- or 5-triazolyl[1,2,4]), (5-tetrazolyl), (2-, 4- or 5-oxazolyl), (3-, 4- or 5-isoxazolyl), (3- or 5-oxadiazolyl[1,2,4]), (2-oxadiazolyl[1,3,4]), (2-thiadiazolyl[1,3,4]), (2-, 4- or 5-thiazolyl), (2-, 4-, or 5-oxazolidinyl), (2-, 4-, or 5-thiazolidinyl), or (2-, 4-, or 5-imidazolidinyl); wherein all of the heterocylic ring systems may be optionally substituted one or more times by $R_{14}$;

Y' is O or S;

$R_7$ is —$(CR_4R_5)_qR_{12}$ or $C_{1-6}$ alkyl wherein the $R_{12}$ or $C_{1-6}$ alkyl group is unsubstituted or substituted one or more times by methyl or ethyl unsubstituted or substituted by 1–3 fluorines, —F, —Br, —Cl, —$NO_2$, —$NR_{10}R_{11}$, —$C(O)R_8$, —$CO_2R_8$, —$O(CH_2)_{2-4}OR_8$, —$O(CH_2)_qR_8$, —CN, —$C(O)NR_{10}R_{11}$, —$O(CH_2)_qC(O)NR_{10}R_{11}$, —$O(CH_2)_qC(O)R_9$, —$NR_{10}C(O)NR_{10}R_{11}$, —$NR_{10}C(O)R_{11}$, —$NR_{10}C(O)OR_9$, —$NR_{10}C(O)R_{13}$, —$C(NR_{10})NR_{10}R_{11}$, —C(NCN)$NR_{10}R_{11}$, —C(NCN)$SR_9$, —$NR_{10}C(NCN)SR_9$, —$NR_{10}C(NCN)NR_{10}R_{11}$, —$NR_{10}S(O)_2R_9$, —$S(O)_{m'}R_9$, —$NR_{10}C(O)C(O)NR_{10}R_{11}$, —$NR_{10}C(O)C(O)R_{10}$, or $R_{13}$;

q is 0, 1, or 2;

$R_{12}$ is $R_{13}$, $C_3$–$C_7$ cycloalkyl, or an unsubstituted or substituted aryl or heteroaryl group selected from the group consisting of (2-, 3- or 4-pyridyl), pyrimidyl, pyrazolyl, (1- or 2-imidazolyl), pyrrolyl, piperazinyl, piperidinyl, morpholinyl, furanyl, (2- or 3-thienyl), quinolinyl, naphthyl, and phenyl;

$R_8$ is independently selected from hydrogen or $R_9$;

$R_9$ is $C_{1-4}$ alkyl unsubstituted or substituted by one to three fluorines;

$R_{10}$ is $OR_8$ or $R_{11}$;

$R_{11}$ is hydrogen, or $C_{1-4}$ alkyl unsubstituted or substituted by one to three fluorines; or when $R_{10}$ and $R_{11}$ are as $NR_{10}R_{11}$ they may together with the nitrogen form a 5 to 7 membered ring comprised only of carbon atoms or carbon atoms and at least one heteroatom selected from O, N, or S;

$R_{13}$ is a substituted or unsubstituted heteroaryl group selected from the group consisting of oxazolidinyl, oxazolyl, thiazolyl, pyrazolyl, triazolyl, tetrazolyl, imidazolyl, imidazolidinyl, thiazolidinyl, isoxazolyl, oxadiazolyl, and thiadiazolyl, and where $R_{13}$ is substituted on $R_{12}$ or $R_{13}$ the rings are connected through a carbon atom and each second $R_{13}$ ring may be unsubstituted or substituted by one or two $C_{1-2}$ alkyl groups unsubstituted or substituted on the methyl with 1 to 3 fluoro atoms;

$R_{14}$ is hydrogen or $R_7$; or when $R_8$ and $R_{14}$ are as $NR_8R_{14}$ they may together with the nitrogen form a 5 to 7 membered ring comprised only of carbon atoms or carbon atoms and at least one heteroatoms selected from O, N, or S;

provided that:
(f) $R_7$ is not $C_{1-4}$ alkyl unsubstituted or substituted by one to three fluorines;

or the pharmaceutically acceptable salts thereof.

This invention also relates to the pharmaceutical compositions comprising a compound of Formula (I) and (II) and a pharmaceutically acceptable carrier or diluent.

The invention also relates to a method of mediation or inhibition of the enzymatic activity (or catalytic activity) of PDE IV in mammals, including humans, which comprises administering to a mammal in need thereof an effective amount of a compound of Formula (I) and (II) as shown below.

The invention further provides a method for the treatment of allergic and inflammatory disease which comprises administering to a mammal, including humans, in need thereof, an effective amount of a compound of Formula (I) and (II).

The invention also provides a method for the treatment of asthma which comprises administering to a mammal, including humans, in need thereof, an effective amount of a compound of Formula (I) and (II).

This invention also relates to a method of inhibiting TNF production in a mammal, including humans, which method comprises administering to a mammal in need of such treatment, an effective TNF inhibiting amount of a compound of Formula (I) and (II). This method may be used for the prophylactic treatment or prevention of certain TNF mediated disease states amenable thereto.

This invention also relates to a method of treating a human afflicted with a human immunodeficiency virus (HIV), which comprises administering to such human an effective TNF inhibiting amount of a compound of Formula (I) and (II).

Compounds of Formula (I) and (II) are also useful in the treatment of additional viral infections, where such viruses are sensitive to upregulation by TNF or will elicit TNF production in vivo.

In addition, compounds of Formula (I) and (II) are also useful in treating yeast and fungal infections, where such yeast and fungi are sensitive to upregulation by TNF or will elicit TNF production in vivo.

DETAILED DESCRIPTION OF THE INVENTION

This invention also relates to a method of mediating or inhibiting the enzymatic activity (or catalytic activity) of PDE IV in a mammal in need thereof and to inhibiting the production of TNF in a mammal in need thereof, which comprises administering to said mammal an effective amount of a compound of Formula (I) and (II).

Phosphodiesterase IV inhibitors are useful in the treatment of a variety of allergic and inflammatory diseases including: asthma, chronic bronchitis, atopic dermatitis, urticaria, allergic rhinitis, allergic conjunctivitis, vernal conjunctivitis, eosinophilic granuloma, psoriasis, rheumatoid arthritis, septic shock, ulcerative colitis, Crohn's disease, reperfusion injury of the myocardium and brain, chronic glomerulonephritis, endotoxic shock and adult respiratory distress syndrome. In addition, PDE IV inhibitors are useful in the treatment of diabetes insipidus and central nervous system disorders such as depression and multi-infarct dementia.

The viruses contemplated for treatment herein are those that produce TNF as a result of infection, or those which are sensitive to inhibition, such as by decreased replication, directly or indirectly, by the TNF inhibitors of Formula (I) and (II). Such viruses include, but are not limited to HIV-1, HIV-2 and HIV-3, cytomegalovirus (CMV), influenza, adenovirus and the Herpes group of viruses, such as, but not limited to, Herpes zoster and Herpes simplex.

This invention more specifically relates to a method of treating a mammal, afflicted with a human immunodeficiency virus (HIV), which comprises administering to such mammal an effective TNF inhibiting amount of a compound of Formula (I) and (II).

The compounds of this invention may also be used in association with the veterinary treatment of animals, other than in humans, in need of inhibition of TNF production. TNF mediated diseases for treatment, therapeutically or prophylactically, in animals include disease states such as those noted above, but in particular viral infections. Examples of such viruses include, but are not limited to feline immunodeficiency virus (FIV) or other retroviral infection such as equine infectious anemia virus, caprine artritis virus, visna virus, maedi virus and other lentiviruses.

The compounds of this invention are also useful in treating yeast and fungal infections, where such yeast and fungi are sensitive to upregulation by TNF or will elicit TNF production in vivo. A preferred disease state for treatment is fungal meningitis. Additionally, the compounds of Formula (I) and (II) may be administered in conjunction with other drugs of choice for systemic yeast and fungal infections. Drugs of choice for fungal infections, include but are not limited to the class of compounds called the polymixins, such as Polymycin B, the class of compounds called the imidazoles, such as clotrimazole, econazole, miconazole, and ketoconazole; the class of compounds called the triazoles, such as fluconazole, and itranazole, and the class of compound called the Amphotericins, in particular Amphotericin B and liposomal Amphotericin B.

The compounds of Formula (I) and (II) may also be used for inhibiting and/or reducing the toxicity of an anti-fungal, anti-bacterial or anti-viral agent by administering an effective amount of a compound of Formula (I) and (II) to a mammal in need of such treatment. Preferably, a compound of Formula (I) and (II) is administered for inhibiting or reducing the toxicity of the Amphotericin class of compounds, in particular Amphotericin B.

The term "$C_{1-3}$ alkyl", "$C_{1-4}$ alkyl", "$C_{1-6}$ alkyl" or "alkyl" groups as used herein is meant to include both straight or branched chain radicals of 1 to 10, unless the chain length is limited thereto, including, but not limited to methyl, ethyl, n-propyl, isopropyl, n-butyl, sec-butyl, isobutyl, tert-butyl, and the like.

"Alkenyl" means both straight or branched chain radicals of 1 to 6 carbon lengths, unless the chain length is limited thereto, including but not limited to vinyl, 1-propenyl, 2-propenyl, or 3-methyl-2-propenyl.

The term "cycloalkyl" or "cycloalkyl alkyl" means groups of 3–7 carbon atoms, such as cyclopropyl, cyclopropylmethyl, cyclopentyl, or cyclohexyl.

"Aryl" or "aralkyl", unless specified otherwise, means an aromatic ring or ring system of 6–10 carbon atoms, such as phenyl, benzyl, phenethyl, or naphthyl. Preferably the aryl is monocyclic, i.e, phenyl. The alkyl chain is meant to include both straight or branched chain radicals of 1 to 4 carbon atoms. "Heteroaryl" means an aromatic ring system containing one or more heteroatoms.

"Halo" means all halogens, i.e., chloro, fluoro, bromo, or iodo.

"Inhibiting the production of IL-1" or "inhibiting the production of TNF" means:

a) a decrease of excessive in vivo IL-1 or TNF levels, respectively, in a human to normal levels or below normal levels by inhibition of the in vivo release of IL-1 by all cells, including but not limited to monocytes or macrophages;

b) a down regulation, at the translational or transcriptional level, of excessive in vivo IL-1 or TNF levels, respectively, in a human to normal levels or below normal levels; or c) a down regulation, by inhibition of the direct synthesis of IL-1 or TNF levels as a postranslational event.

The phrase "TNF mediated disease or disease states" means any and all disease states in which TNF plays a role, either by production of TNF itself, or by TNF causing another cytokine to be released, such as but not limited to IL-1 or IL-6. A disease state in which IL-1, for instance is a major component, and whose production or action, is exacerbated or secreted in response to TNF, would therefore be considered a disease state mediated by TNF. As TNF-β (also known as lymphotoxin) has close structural homology with TNF-α (also known as cachectin), and since each induces similar biologic responses and binds to the same cellular receptor, both TNF-α and TNF-β are inhibited by the compounds of the present invention and thus are herein referred to collectively as "TNF" unless specifically delineated otherwise. Preferably TNF-α is inhibited.

"Cytokine" means any secreted polypeptide that affects the functions of cells, and is a molecule which modulates interactions between cells in immune, inflammatory, or hematopoietic responses. A cytokine includes, but is not limited to, monokines and lymphokines regardless of which cells produce them. The cytokine inhibited by the present invention for use in the treatment of a HIV-infected human must be a cytokine which is implicated in (a) the initiation and/or maintenance of T cell activation and/or activated T cell-mediated HIV gene expression and/or replication, and/ or (b) any cytokine-mediated disease associated problem such as cachexia or muscle degeneration. Preferrably, his cytokine is TNF-α.

All of the compounds of Formula (I) and (II) are useful in the method of inhibiting the production of TNF, preferably by macrophages, monocytes or macrophages and monocytes, in a mammal, including humans, in need thereof. All of the compounds of Formula (I) and (II) are useful in the method of inhibiting or mediating the enzymatic or catalytic activity of PDE IV and in treatment of disease states mediated thereby.

Preferred compounds are as follows:

When $R_1$ for the compounds of Formula (I) and (II) is an alkyl substituted by 1 or more halogens, the halogens are preferably fluorine and chlorine, more preferably a $C_{1-4}$ alkyl substituted by 1 or more fluorines. The preferred halo-substituted alkyl chain length is one or two carbons, and most preferred are the moieties —$CF_3$, —$CH_2F$, —$CHF_2$, —$CF_2CHF_2$, —$CH_2CF_3$, and —$CH_2CHF_2$. Preferred $R_1$ substitutents for the compounds of Formula (I) and (II) are $CH_2$-cyclopropyl, $CH_2$-$C_{5-6}$ cycloalkyl, $C_{4-6}$ cycloalkyl unsubstituted or substituted with OH, $C_{7-11}$ polycycloalkyl, (3- or 4-cyclopentenyl), phenyl, tetrahydrofaran-3-yl, benzyl or $C_{1-2}$ alkyl unsubstituted or substituted by 1 or more fluorines, —$(CH_2)_{1-3}C(O)O(CH_2)_{0-2}CH_3$, —$(CH_2)_{1-3}O(CH_2)_{0-2}CH_3$, and —$(CH_2)_{2-4}OH$.

When the $R_1$ term is ($CR_4R_5$), the $R_4$ and $R_5$ terms are independently hydrogen or alkyl. This allows for branching of the individual methylene units as $(CR_4R_5)_n$ or $(CR_4R_5)_m$; each repeating methylene unit is independent of the other, e.g., $(CR_4R_5)_n$ wherein n is 2 can be —$CH_2CH(-CH_3)$—, for instance. The individual hydrogen atoms of the repeating methylene unit or the branching hydrocarbon can be unsubstituted or be substituted by fluorine independent of each other to yield, for instance, the preferred $R_1$ substitutions, as noted above.

When $R_1$ is a $C_{7-11}$ polycycloalkyl, examples are bicyclo [2.2.1]-heptyl, bicyclo[2.2.2]octyl, bicyclo[3.2.1]octyl, tricyclo[5.2.1.0$^{2.6}$]decyl, etc. additional examples of which are described in Saccamano et al., WO 87/06576, published 5 Nov. 1987, whose disclosure is incorporated herein by reference in its entirety.

Preferred Z terms are O, NCN, $NR_7$, $NOR_{14}$, $NOR_{15}$, $NNR_4R_{14}$, $NNR_4R_{15}$, 2-(1,3-dithiane), dimethylthio ketal, 2-(1,3-dioxolane), or dimethyl ketal. More preferred are O, $NR_7$, $NOR_{14}$, $NOR_{15}$, and 2-(1,3-dioxolane).

Preferred X groups for Formula (I) and (II) are those wherein X is $YR_2$ and Y is oxygen. The preferred $X_2$ group for Formula (I) and (II) is that wherein $X_2$ is oxygen. The preferred $X_3$ group for Formula (I) and (II) is that wherein $X_3$ is hydrogen. Preferred $R_2$ groups, where applicable, is a $C_{1-2}$ alkyl unsubstituted or substituted by 1 or more halogens. The halogen atoms are preferably fluorine and chlorine, more preferably fluorine. More preferred $R_2$ groups are those wherein $R_2$ is methyl, or the fluoro-substituted alkyls, specifically a $C_{1-2}$ alkyl, such as a —$CF_3$, —$CHF_2$, or —$CH_2CHF_2$ moiety. Most preferred are the —$CHF_2$ and —$CH_3$ moieties.

Preferred $R_7$ moieties include $R_{13}$, unsubstituted or substituted —$(CH_2)_{0-2}$(2-, 3- or 4-pyridyl), $(CH_2)_{1-2}$(2-imidazolyl), $(CH_2)_2$(4-morpholinyl), $(CH_2)_2$(4-piperazinyl), $(CH_2)_{1-2}$(2-thienyl), $(CH_2)_{1-2}$(4-thiazolyl), unsubstituted or substituted pyrimidinyl, and substituted or unsubstituted $(CH_2)_{0-2}$phenyl.

Preferred rings when $R_{10}$ and $R_{11}$ in the moiety —$NR_{10}R_{11}$ together with the nitrogen to which they are attached form a 5 to 7 membered ring comprised only of carbon atoms or carbon atoms and at least one heteroatom selected from O, N, or S include, but are not limited to 1-imidazolyl, 2-($R_8$)-1-imidazolyl, 1-pyrazolyl, 3-($R_8$)-1-pyrazolyl, 1-triazolyl, 2-triazolyl, 5-($R_8$)-1-triazolyl, 5-($R_8$)-2-triazolyl, 5-($R_8$)-1-tetrazolyl, 5-($R_8$)-2-tetrazolyl, 1-tetrazolyl, 2-tetrazolyl, morpholinyl, piperazinyl, 4($R_8$)-1-piperazinyl, or pyrrolyl ring.

Preferred rings when $R_8$ and $R_{14}$ in the moiety —$NR_8R_{14}$ together with the nitrogen to which they are attached may form a 5 to 7 membered ring comprised only of carbon atoms or carbon atoms and at least one heteroatom selected from O, N, or S include, but are not limited to 1-imidazolyl, 1-pyrazolyl, 1-triazolyl, 2-triazolyl, 1-tetrazolyl, 2-tetrazolyl, morpholinyl, piperazinyl, and pyrrolyl. The respective rings may be additionally substituted, where applicable, on an available nitrogen or carbon by the moiety $R_7$ as described herein for Formula (I) and (II). Illustrations of such carbon substitutions includes, but is not limited to, 2-($R_7$)-1-imidazolyl, 4($R_7$)-1-imidazolyl, 5-($R_7$)-1-imidazolyl, 3-($R_7$)-1-pyrazolyl, 4-($R_7$)-1-pyrazolyl, 5-($R_7$)-1-pyrazolyl, 4-($R_7$)-2-triazolyl, 5-($R_7$)-2-triazolyl, 4-($R_7$)-1-triazolyl, 5-($R_7$)-1-triazolyl, 5-($R_7$)-1-tetrazolyl, and 5-($R_7$)-2-tetrazolyl. Applicable nitrogen substitution by $R_7$ includes, but is not limited to, 1-($R_7$)-2-tetrazolyl, 2-($R_7$)-1-tetrazolyl, 4-($R_7$)-1-piperazinyl. Where applicable, the ring may be substituted one or more times by $R_7$.

Preferred groups for $NR_8R_{14}$ which contain a heterocyclic ring are 5-($R_{14}$)-1-tetrazolyl, 2-($R_{14}$)-1-imidazolyl, 5-($R_{14}$) -2-tetrazolyl, 4-($R_{14}$)-1-piperazinyl, or 4-($R_{15}$)-1-piperazinyl.

Preferred rings for $R_{13}$ include (2-, 4- or 5-imidazolyl), (3-, 4- or 5-pyrazolyl), (4- or 5-triazolyl[1,2,3]), (3- or 5-triazolyl[1,2,4]), (5-tetrazolyl), (2-, 4- or 5-oxazolyl), (3-, 4- or 5-isoxazolyl), (3- or 5-oxadiazolyl[1,2,4]), (2-oxadiazolyl[1,3,4]), (2-thiadiazolyl[1,3,4]), (2-, 4-, or 5-thiazolyl), (2-, 4-, 5-oxazolidinyl), (2-, 4-, or 5-thiazolidinyl), or (2-, 4-, or 5-imidazolidinyl).

When the $R_7$ group is unsubstituted or substituted by a heterocyclic ring such as imidazolyl, pyrazolyl, pyrimidinyl, triazolyl, tetrazolyl, or thiazolyl, the heterocyclic ring itself may be unsubstituted or substituted by $R_8$ either on an available nitrogen or carbon atom, such as 1-($R_8$)-2-imidazolyl, 1-($R_8$)-4-imidazolyl, 1-($R_8$)-5-imidazolyl, 1-($R_8$)-3-pyrazolyl, 1-($R_8$)-4-pyrazolyl, 1-($R_8$)-5-pyrazolyl, 1-($R_8$)-4-triazolyl, or 1-($R_8$)-5-triazolyl. Where applicable, the ring may be substituted one or more times by $R_8$.

W is preferably alkyl, alkenyl or alkynyl of 3 to 5 carbon atoms, and where it is alkenyl or alkynyl, that one or two double or triple bonds be present. It is most preferred that W is ethynyl or 1,3-butadiynyl.

Preferred are those compounds of Formula (I) and (II) wherein $R_1$ is —$CH_2$-cyclopropyl, —$CH_2$—$C_{5-6}$ cycloalkyl, —$C_{4-6}$ cycloalkyl unsubstituted or substituted with OH, tetrahydrofuran-3-yl, (3- or 4-cyclopentenyl), benzyl or —$C_{1-2}$ alkyl unsubstituted or substituted by 1 or more fluorines, and —$(CH_2)_{2-4}$ OH; $R_2$ is methyl or fluoro-substituted alkyl, $R_3$ is $R_7$ where $R_7$ is an unsubstituted or substituted aryl or heteroaryl ring, X is $YR_2$, and Z is O, $NR_7$.

Z' is preferably $COOR_{14}$.

Most preferred are those compounds wherein $R_1$ is —$CH_2$-cyclopropyl, cyclopentyl, 3-hydroxycyclopentyl, methyl or $CF_2H$; X is $YR_2$; Y is oxygen; $X_2$ is oxygen; $X_3$ is hydrogen; and $R_2$ is $CF_2H$ or methyl, W is ethynyl or 1,3-butadiynyl, $R_3$ is a substituted or unsubstituted pyrimidinyl ring, and Z is O, $NR_7$.

Pharmaceutically acceptable salts of the instant compounds, where they can be prepared, are also intended to be covered by this invention. These salts will be ones which are acceptable in their application to a pharmaceutical use. By that it is meant that the salt will retain the biological activity of the parent compound and the salt will not have untoward or deleterious effects in its application and use in treating diseases.

Pharmaceutically acceptable salts are prepared in a standard manner. The parent compound, dissolved in a suitable solvent, is treated with an excess of an organic or inorganic acid, in the case of acid addition salts of a base, or an excess of organic or inorganic base where the molecule contains a COOH for example.

Pharmaceutical compositions of the present invention comprise a pharmaceutical carrier or diluent and some amount of a compound of the Formula (I) and (II). The compound may be present in an amount to effect a physiological response, or it may be present in a lesser amount such that the user will need to take two or more units of the composition to effect the treatment intended. These compositions may be made up as a solid, liquid or in a gaseous form. Or one of these three forms may be transformed to another at the time of being administered such as when a solid is delivered by aerosol means, or when a liquid is delivered as a spray or aerosol.

The nature of the composition and the pharmaceutical carrier or diluent will, of course, depend upon the intended route of administration, for example parenterally, topically, orally or by inhalation.

For topical administration the pharmaceutical composition will be in the form of a cream, ointment, liniment, lotion, pastes, aerosols, and drops suitable for administration to the skin, eye, ear, or nose.

For parenteral administration the pharmaceutical composition will be in the form of a sterile injectable liquid such as an ampule or an aqueous or non-aqueous liquid suspension.

For oral administration the pharmaceutical composition will be in the form of a tablet, capsule, powder, pellet, atroche, lozenge, syrup, liquid, or emulsion.

When the pharmaceutical composition is employed in the form of a solution or suspension, examples of appropriate pharmaceutical carriers or diluents include: for aqueous systems, water, for non-aqueous systems, ethanol, glycerin, propylene glycol, corn oil, cottonseed oil, peanut oil, sesame oil, liquid parafins and mixtures thereof with water, for solid systems, lactose, kaolin and mannitol; and for aerosol systems, dichlorodifluoromethane, chlorotrifluoroethane and compressed carbon dioxide. Also, in addition to the pharmaceutical carrier or diluent, the instant compositions may include other ingredients such as stabilizers, antioxidants, preservatives, lubricants, suspending agents, viscosity modifiers and the like, provided that the additional ingredients do not have a detrimental effect on the therapeutic action of the instant compositions.

The pharmaceutical preparations thus described are made following the conventional techniques of the pharmaceutical chemist as appropriate to the desired end product.

In these compositions, the amount of carrier or diluent will vary but preferably will be the major proportion of a suspension or solution of the active ingredient. When the diluent is a solid it may be present in lesser, equal or greater amounts than the solid active ingredient.

Usually a compound of formula I is administered to a subject in a composition comprising a nontoxic amount sufficient to produce an inhibition of the symptoms of a disease in which leukotrienes are a factor. Topical formulations will contain between about 0.01 to 5.0% by weight of the active ingredient and will be applied as required as a preventative or curative agent to the affected area. When employed as an oral, or other ingested or injected regimen, the dosage of the composition is selected from the range of from 50 mg to 1000 mg of active ingredient for each administration. For convenience, equal doses will be administered 1 to 5 times daily with the daily dosage regimen being selected from about 50 mg to about 5000 mg.

It will be recognized that some of the compounds of Formula (I) and (II) may exist in both racemic and optically active forms; some may also exist in distinct diastereomeric forms possessing distinct physical and biological properties. All of these compounds are considered to be within the scope of the present invention.

Compounds of Formula (I) where Z is O or (II) may exist in a tautomeric form, such as the enol form. This may be represented by the =O being exocyclic to the cyclohexane ring (or

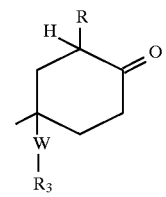

as contrasted to the endocyclic or —C(—OH)=C(—R)— moiety wherein the cyclohexane ring is now unsaturated in the 1-2 position, i.e. cyclohex-1-ene, or

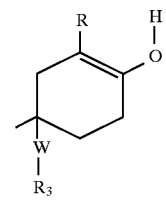

and R is Z in Formula (II). It is also recognized that the 2-position of the ring in the exocyclic form can be substituted (R) such as in the compounds of Formula (I) or (II).

The following examples are given to ftuther illustrate the described invention. These examples are intented solely for illustrating the invention and should not be read to limit the invention in any manner. Reference is made to the claims for what is reserved to the inventors hereunder.

No unacceptable toxicological effects are expected when these compounds are administered in accordance with the present invention.

Methods Of Preparation

Synthetic Scheme(s) With Textual Description

Compounds of Formula (I) may be prepared by the processes disclosed herein which comprise reacting a terminal acetylene as, e.g., compound 1-Scheme 1, with an aryl halide, such as phenyl iodide, in the presence of a suitable catalyst, such as a copper(I) halide and a bivalent or zerovalent palladium compound in the presence of, e.g., triphenylphosphine, in a suitable solvent, such as an amine, as in the procedure of Brandsma et al. (Syn. Comm., 1990, 20, 1889), followed by hydrolysis of the ketal protecting group under standard conditions, provides a compound of the Formula 2-Scheme 1. Compounds of the Formula 1-Scheme 1 may be prepared by procedures analogous to those described in prior filed co-pending U.S. application Ser. Nos. 07/862,083, 07/968,753 and PCT/US93/01990 designating the United States and filed 05 Mar. 1993 (WIPO publication No. WO 93/19748) or PCT application PCT/US93/02325 published as WO 93/19750.

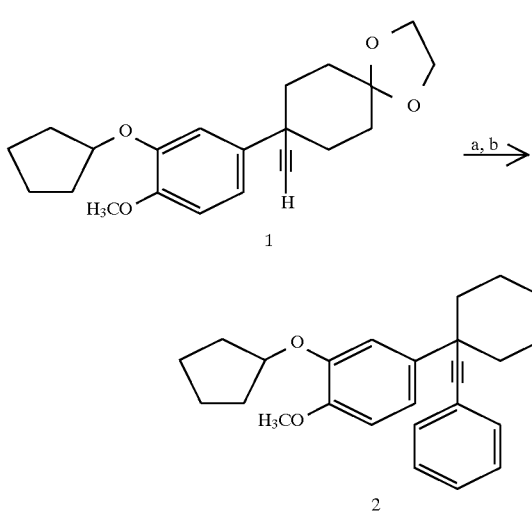

a) Pd(PPh$_3$)$_4$, PPh$_3$, CuI, C$_6$H$_5$I, piperidine;
b) pyridinium p-toluenesulfonate, (H$_3$C)$_2$CO/H$_2$O Alternatively, compounds of Formula (I) may be prepared by reacting a terminal acetylene as, e.g., compound 1-Scheme 2, with an appropriate halide, R$_3$X, wherein R$_3$ represents R$_3$ as defined in relation to Formula (I) or a group convertible to R$_3$, in the presence of a suitable catalyst, such as a copper(I) halide and a bivalent or zerovalent palladium compound in the presence of, e.g., triphenylphosphine, in a suitable solvent, such as an amine, as in the procedure of Brandsma et al. (Syn. Comm., 1990, 20, 1889), to provide a compound of the Formula 2-Scheme 2; such compounds of the Formula (I) may then be converted to other compounds of the Formula (I) by standard manipulation of the functional groups on the R$_3$ moiety. Compounds of the Formula 1-Scheme 2 may be prepared by procedures analogous to those described in prior filed co-pending U.S. application Ser. Nos. 07/862,083, 07/968,753 and PCT/US93/01990 designating the United States and filed 05 Mar. 1993 (WIPO publication No. WO 93/19748) or PCI application PCT/US93/02325 published as WO 93/19750.

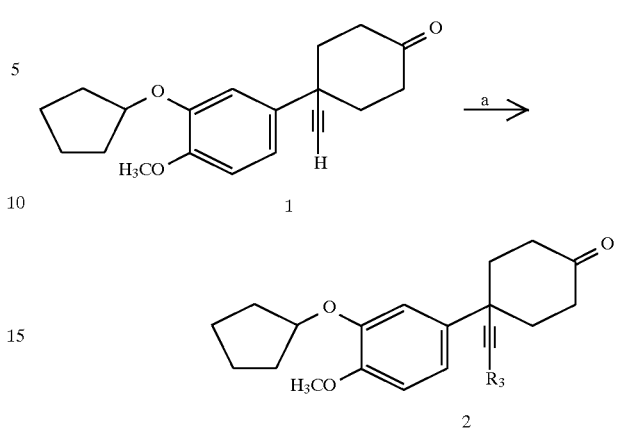

a) Pd(PPh$_3$)$_4$, PPh$_3$, CuI, R$_3$X, piperidine

Alternatively, oxidative carbonylation of a terminal acetylene as, e.g., compound 1-Scheme 3, using an appropriate metal salt, such as a copper salt with a catalytic amount of a palladium salt, in the presence of a suitable base as an acid trap, such as sodium acetate, in a suitable alcohol, such as methanol, as in the method of Tsuji et al. (Tet. Lett., 1980, 21, 849), followed by hydrolysis of the methyl ester under standard conditions, then provides the compound of the Formula (I) (2-Scheme 3); such compounds of the Formula (I) may then be converted to other compounds of the Formula (I) by standard manipulation of the carboxylic ester moiety.

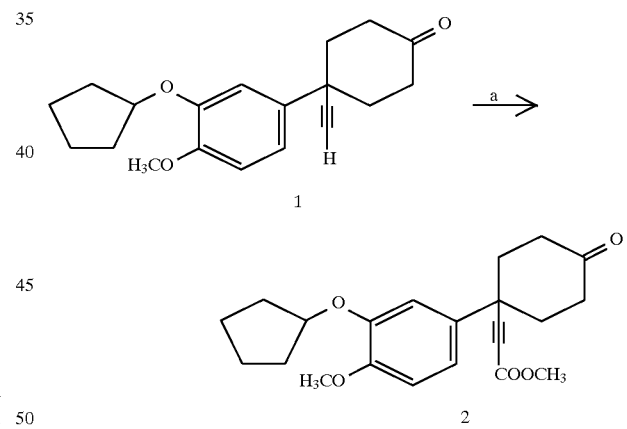

a) PdCl$_2$, CuCl$_2$, NaO$_2$CCH$_3$, CO, CH$_3$OH

Compounds of Formula (II) may be prepared by processes analogous to those in Schemes 1, 2 and 3 above, as illustrated in Scheme 4 wherein. Depending upon the exact nature of the Z' groups of the compounds of the Formula (II), the =O group may require protection during the coupling steps described herein as, e.g., a compound of the Formula (II) wherein =O is a dimethyl ketal or 2-(1,3-dioxolane), followed by deprotection and then reaction by the synthetic procedures described in prior filed co-pending U.S. application Ser. Nos. 07/862,083, 07/968,753 and PCT/US93/01990 designating the United States and filed 05 Mar. 1993 (WIPO publication No. WO 93/19748) or PCT application PCT/US93/02325 published as WO 93/19750, to provide the Formula (II) compound; likewise, the Z' group may require protection during the coupling steps, followed by deprotection to provide the Formula (II) compound and such protective groups are well known to those skilled in the art. (See: Greene, T. and Wuts, P. G. M., Protecting Groups in Organic Synthesis, 2nd Ed., John Wiley and Sons, New York, 1991.)

Scheme 4

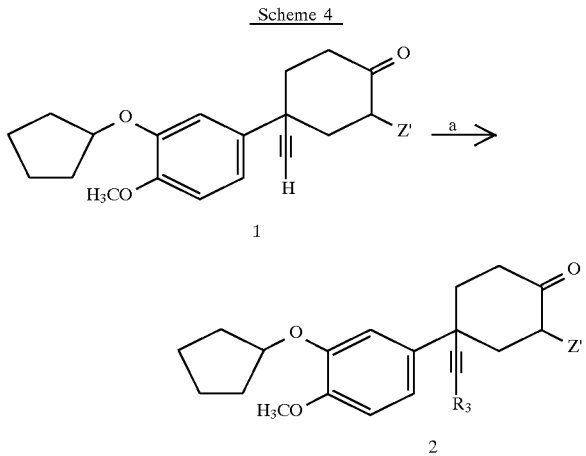

a) Pd(PPh$_3$)$_4$, PPh$_3$, CuI, R$_3$X, piperidine

Preparation of the remaining compounds of the Formulas (I) and (II) may be accomplished by procedures analogous to those described above and in the Examples, infra.

It will be recognized that compounds of the Formulas (I) and (II) may exist in distinct diastereomeric forms possessing distinct physical and biological properties; such isomers may be separated by standard chromatographic methods.

The following examples are given to further illustrate the described invention. These examples are intented solely for illustrating the invention and should not be read to limit the invention in any manner. Reference is made to the claims for what is reserved to the inventors hereunder.

Synthetic examples

EXAMPLE 1

Preparation of 4-(3-cyclopentyloxy-4-methoxyphenyl-1,1-(ethylenedioxy)-4-(2-pyridylethynyl)cyclohexane 1a) 4-cyano-4-(3-cyclopentyloxy-4-methoxyphenyl)-1,1-(ethylenedioxy)cyclohexane A solution of 4-cyano-4-(3-cyclopentyloxy-4-methoxyphenyl)cyclohexan-1-one (1.0 g, 3.19 mmol, prepared by the procedures described in PCT applications PCT/US3/01990 (WIPO publication No. WO 93/19748) and PCT application PCT/US93/02325 published as WIPO number WO 93/19750) in benzene (25 mL) was treated with p-toluenesulfonic acid (5 mg) and ethylene glycol (0.18 mL, 3.19 mmol) and was heated to reflux under an argon atmosphere; water was removed from the mixture via a Dean-Stark trap. After 1.5 h, ether (200 mL) was added, the solution was washed with aqueous 5% sodium bicarbonate and brine, was dried (potassium carbonate) and was evaporated to provide a clear colorless oil. $^1$H NMR(250 MHz, CDCl$_3$) δ 7.0 (m, 2H), 6.85 (d, J=7 Hz, 1H), 4.8 (m, 1H), 4.0 (m, 4H), 3.85 (s, 3H), 1.58–2.20 (m, 16H).

1b) 4-(3-cyclopentyloxy-4-methoxyphenyl)-1,1-(ethylenedioxy)-4-formylcyclohexane Diisobutylaluminum hydride (1.0M in toluene, 8.13 mL, 8.13 mmol) was added dropwise to a solution of 4-cyano-4-(3-cyclopentyloxy-4-methoxyphenyl)-1,1-(ethylenedioxy)cyclohexane (1.16 g, 3.19 mmol) dissolved in toluene (20 mL) under an argon atmosphere. After 18 h at room temperature, saturated aqueous sodium bisulfite (100 mL) was added and the mixture was extracted three times with dichloromethane. The combined organic extract was washed with brine, was dried (potassium carbonate) and was evaporated. Purification by flash chromatography, eluting with 4:1 hexanes/ethyl acetate, provided a clear colorless oil. $^1$H NMR(400 MHz, CDCl$_3$) δ 9.35 (s, 1H), 6.88 (br s, 2H), 6.80 (s, 1H), 4.73 (m, 1H), 3.95 (m, 4H), 3.85 (s, 3H), 2.33 (m, 2H), 2.10 (m, 2H), 1.57–1.99 (m, 12H).

1c) 4-(3-cyclopentyloxy-4-methoxyphenyl)-1,1-(ethylenedioxy)-4-ethynylcyclohexane A solution of dimethyl (diazomethyl)phosphonate (0.516 g, 3.44 mmole, prepared as in Seyferth, D.; Marmor, R. S.; Hilbert, P. J. Org. Chem 1971, 36(10), 1379–1386) dissolved in dry tetrahydrofuran (10 mL) was added via cannulation to a solution of potassium t-butoxide (0.386 g, 3.4 mmol) dissolved in dry tetrahydrofuran (10 mL) at −78° C. under an argon atmosphere. To this was added rapidly a solution of 4-(3-cyclopentyloxy-4-methoxyphenyl)-1,1-(ethylenedioxy)-4-formylcyclohexane (0.62 g, 1.72 mmol) in dry tetrahydrofuran (10 mL). After 2 h, the reaction was warmed to room temperature, water was added and the mixture was extracted three times with ethyl acetate. The combined organic extract was washed with brine, was dried (sodium sulfate) and was evaporated. Purification by flash chromatography, eluting with 3:1 hexanes/ethyl acetate provided a white solid. mp 53.5°–55° C.

1d) 4-(3-cyclopentyloxy-4-methoxyphenyl)-1,1-(ethylenedioxy)-4-(2-pyridylethynyl)cyclohexane To a solution of 4-(3-cyclopentyloxy-4-methoxyphenyl)-1,1-(ethylenedioxy)-4-ethynylcyclohexane (0.15 g, 0.42 mmol) and 2-bromopyridine (0.040 mL, 0.42 mmol) in piperidine (2 mL) under an argon atmosphere were added tetrakis(triphenylphosphine)-palladium(0) (0.02 g, 4%), copper(I) iodide (0.005 g, 6%) and a small crystal of triphenylphosphine, and the mixture was heated at 80° C. for 0.5 h. Water was added and the mixture was extracted three times with dichloromethane, the extract was dried (magnesium sulfate) and was evaporated. Purification by flash chromatography, eluting with 35:65 ethyl acetate:hexanes, provided 4-(3-cyclopentyloxy-4-methoxyphenyl)-1,1-(ethylenedioxy)-4-(2-pyridylethynyl) cyclohexane as a white foam. mp 41°–42° C. $^1$H-NMR (400 MHz, CDC$_3$) δ 8.58 (d, J=4.6 Hz, 1H), 7.65 (t, J=7.7 Hz, 1H), 7.43 (d, J=8.0 Hz, 1H), 7.21 (m, 2H), 7.17 (d, J=8.5 Hz, 1H), 6.84 (d, J=8.5 Hz, 1H), 4.81 (m, 1H), 3.99 (s, 4H), 3.84 (s, 3H), 2.25 (m, 2H), 2.15 (m, 4H), 1.8–2.0 (m, 8H), 1.59 (m, 2H).

EXAMPLE 2

Preparation of 4-(3-cyclopentyloxy-4-methoxyphenyl)-1,1-(ethylenedioxy)-4-(phenylethynyl)cyclohexan-1-one A sample of 1,1-(ethylenedioxy)-4-(3-cyclopentyloxy-4-methoxyphenyl)-4-methynylcyclohexane (0.15 g, 0.42 mmol) was treated with trace amounts of triphenylphosphine, tetrakis(triphenylphosphine)palladium (0) and copper(I) iodide. Iodobenzene (0.47 mL, 4.2 mmol) and piperidine (2 mL) were then added and the mixture was heated under an argon atmosphere. After 3 h, the mixture was diluted with ethyl acetate (50 mL), was washed once with dilute aqueous HCl, was dried (magnesium sulfate) and was evaporated. Purification by flash chromatography (4:1 hexanes/ethyl acetate) provided a clear colorless oil. $^1$H NMR(400 MHz, CDCl$_3$) δ 7.44 (m, 2H), 7.3 (m, 3H), 7.23

(d, J=2 Hz, 1H), 7.12 (dd, J=2 and 8 Hz, 1H), 6.81 (d, J=8 Hz, 1H), 4.8 (m, 1H), 4.0 (s, 4H), 3.85 (s, 3H), 2.25 (m, 2H), 2.10 (m, 2H), 1.78–2.03 (m, 10H), 1.6 (m, 2H).

EXAMPLE 3

Preparation of 4-(3-cyclopentyloxy-4-methoxyphenyl)-4-(2-phenylethynyl)cyclohexan-1-one To a solution of 4-(3-cyclopentyloxy-4-methoxyphenyl)-1,1-(ethylenedioxy)4-(phenylethynyl)cyclohexan-1-one (0.18 g, 0.42 mmol) dissolved in 4:1 acetone/water (5 mL) was added pyridinium p-toluenesulfonate (5 mg). The mixture was heated to reflux under an argon atmosphere. After 6 h, water (15 mL) was added and the mixture extracted three times with ethyl acetate. The combined organic extract was dried (magnesium sulfate) and was evaporated. Purification by trituration from ether/hexanes provided a white solid. mp 99°–100° C.

EXAMPLE 4

Preparation of 4-(3-cyclopentyloxy-4-methoxyphenyl)-4-(2-pyridylethynyl)cyclohexan-1-one A mixture of 4-(3-cyclopentyloxy-4-methoxyphenyl)-1,1-(ethylenedioxy)-4-(2-pyridylethynyl)cyclohexane (0.17 g, 0.39 mmol) and pyridinium p-toluenesulfonate (0.10 g, 0.39 mmol) in acetone (4 mL) and water (1 mL) was refluxed for three days, then was evaporated. Water was added, the mixture was extracted three times with dichloromethane, the extract was dried (magnesium sulfate) and was evaporated. Purification by flash chromatography, eluting with 25:75 ethyl acetate:hexanes, provided 4-(3-cyclopentyloxy-4-methoxyphenyl)-4-(2-pyridylethynyl)cyclohexan-1-one as a wax. $^1$H-NMR (400 MHz, CDCl$_3$) δ 8.61 (d, J=4.8 Hz, 1H), 7.68 (dt, J=7.8, 1.8 Hz, 1H), 7.47 (d, J=7.8 Hz, 1H), 7.27 (m, 1H), 7.20 (d, J=2.3 Hz, 1H), 7.15 (dd, J=8.5, 2.4 Hz, 1H), 6.87 (d, J=8.5 Hz, 1H), 4.81 (m, 1H), 3.85 (s, 3H), 3.07 (dt, J=14.4, 5.8 Hz, 2H), 2.49 (d, J=14.8 Hz, 2H), 2.41 (m, 2H), 2.27 (dt, J=13.4, 3.9 Hz, 2H), 1.8–2.0 (m, 6H), 1.61 (m, 2H). Anal. (C$_{25}$H$_{27}$NO$_3$.0.65 H$_2$O) calcd: C, 74.84; H, 7.11; N, 3.49; found: C, 75.00; H, 6.83; N, 3.52.

EXAMPLE 5

Preparation of 4-(3-cyclopentyloxy-4-methoxyphenyl)-1,1-(ethylenedioxy)-4-(4-nitrophenylethynyl)cyclohexane To a solution of 4-(3-cyclopentyloxy-4-methoxyphenyl)-1,1-(ethylenedioxy)-4-ethynylcyclohexane (0.15 g, 0.42 mmol) and 4-iodonitrophenol (0.11 g, 0.42 mmol) in piperidine (2 mL) under an argon atmosphere were added tetrakis(triphenylphosphine)palladium(0) (0.02 g, 4%), copper(I) iodide (0.005 g, 6%) and a small crystal of triphenylphosphine. After heating at 80° C. for 0.5 h, water and 1N hydrochloric acid were added. The mixture was extracted three times with dichloromethane, the extract was dried (magnesium sulfate) and was evaporated. Purification by flash chromatography, eluting with 2:8 ethyl acetate:hexanes, provided 4-(3-cyclopentyloxy-4-methoxyphenyl)-1,1-(ethylenedioxy)-4-(4-nitrophenylethynyl)cyclohexane as a red-orange wax. mp 58°–59° C. $^1$H-NMR (400 MHz, CDCl$_3$) δ 8.18 (d, J=8.7 Hz, 2H), 7.58 (d, J=8.7 Hz, 2H), 7.16 (d, J=2.5 Hz, 1H), 7.12 (dd, J=8.4, 2.5 Hz, 1H), 6.86 (d, J=8.4 Hz, 1H), 4.80 (m, 1H), 4.01 (s, 4H), 3.85 (s, 3H), 1.8–2.3 (m, 14H), 1.6 (m, 2H).

EXAMPLE 6

Preparation of 4-(3-cyclopentyoxy-4-methoxyphenyl)-4-(4-aminophenylethynyl)cyclohexan-1-one To 4-(3-cyclopentyloxy-4-methoxyphenyl)-1,1-(ethylenedioxy)-4-(4-nitrophenylethynyl)cyclohexane (0.19 g, 0.40 mmol) in methanol (1 mL), acetic acid (1.2 mL), and water (1.2 mL) under an argon atmosphere was added titanium trichloride (0.3 g, 2 mmol). After stiring for 1.5 h at room temperature, water (1.2 mL) and ammonium hydroxide (2.5 mL) were added. After stirring an additional 1 h, methanol (17.5 mL), 5% sodium carbonate (17.5 mL) and dichloromethane (35 mL) were added, and stirring was continued for 3 days. The suspension was filtered through Celite®, was washed well with dichloromethane, and was evaporated. Water was added, the mixture was extracted three times with dichloromethane, the extract was dried (magnesium sulfate) and was evaporated. Purification by flash chromatography, eluting with 3:7 ethyl acetate:hexanes, provided 4-(3-cyclopentyloxy-4-methoxyphenyl)-4-(4-aminophenylethynyl)cyclohexan-1-one as a colorless oil. $^1$H-NMR (400 MHz, CDCl$_3$) δ 7.28 (d, J=8.4 Hz, 2H), 7.24 (d, J=2.1 Hz, 1H), 7.12 (d, J=8.5 Hz, 1H), 6.85 (d, J=8.5 Hz, 1H), 6.64 (d, J=8.1 Hz, 2H), 4.80 (m, 1H), 3.85 (s, 3H), 3.05 (dt, J=14.3, 4.1 Hz, 2H), 2.45 (br d, J=14.6 Hz, 2H), 2.29 (m, 4H), 1.8–2.0 (m, 6H), 1.61 (m, 2H).

EXAMPLE 7

Prepartion of 4-(3-cyclopentyloxy-4-methoxyphenyl)-4-(4-acetamidophenylethynyl)cyclohexan-1-one To 4-(3-cyclopentyloxy-4-methoxyphenyl)-4-(4-amicophenylethynyl)cyclohexan-1-one (0.12 g, 0.29 mmol) in dichloromethane (3 mL) under an argon atmosphere were added pyridine (five drops) and acetic anhydride (0.081 mL, 0.86 mmol) and the reaction was stirred at room temperature for 2 h. Hydrochloric acid (1N) was added, the mixture was extracted three times with dichloromethane, the extract was dried (magnesium sulfate) and was evaporated. Purification by flash chromatography, eluting with 1:1 ethyl acetate:hexanes, provided 4-(3-cyclopentyloxy-4-methoxyphenyl)-4-(4-acetamidophenylethynyl)cyclohexan-1-one as a white solid. mp 79°–80° C.; Anal. (C$_{28}$H$_{31}$NO$_4$.0.5 H$_2$O) calcd: C, 73.98; H, 7.10; N, 3.08; found: C, 74.11; H, 7.24; N, 3.03.

EXAMPLE 8

Preparation of 4-(3-cyclopentyloxy-4-methoxyphenyl)-1,1-(ethylenedioxy)-4-(3-nitrophenylethynyl)cyclohexane To a solution of 4-(3-cyclopentyloxy-4-methoxyphenyl)-1,1-(ethylenedioxy)-4-ethynylcyclohexane (0.14 g, 0.38 mmol) and 3-iodonitrophenol (0.10 g, 0.38 mmol) in piperidine (2 mL) under an argon atmosphere were added tetrakis(triphenylphosphine)palladium(0) (0.02 g, 4%), copper(I) iodide (0.005 g, 6%) and a small crystal of triphenylphosphine. After heating at 70° C. for 0.33 h, the mixture was diluted with dichloromethane, was washed with 1N hydrochloric acid, was dried (magnesium sulfate) and was evaporated. Purification by flash chromatography, eluting with 2:8 ethyl acetate:hexanes, provided 1,1-(ethylenedioxy)-4-(3-cyclopentyloxy-4-methoxyphenyl)-4-

(3-nitrophenylethynyl)cyclohexane as an orange wax. $^1$H-NMR (400MHz, CDCl$_3$) δ 8.29 (s, 1H), 8.16 (d, J=9.0 Hz, 1H), 7.75 (d, J=7.9 Hz, 1H), 7.50 (t, J=8.0 Hz, 1H), 7.26 (d, J=2 Hz, 1H), 7.14 (dd, J=8.3, 2 Hz, 1H), 6.86 (d, J=8.3 Hz, 1H), 4.82 (m, 1H), 4.01 (s, 4H), 3.85 (s, 3H), 2.18 (m, 4H), 2.07 (m, 2H), 1.93 (m, 4H), 1.85 (m, 4H), 1.6 (m, 2H).

EXAMPLE 9

Preparation of 4-(3-cyclopentyloxy-4-methoxyphenyl)-4-(3-aminophenylethynyl)cyclohexan-1-one To 4-(3-cyclopentyloxy-4-methoxyphenyl)-1,1-(ethylenedioxy)-4-(3-nitrophenylethynyl)cyclohexane (0.17 g, 0.35 mmol) in methanol (1 mL), acetic acid (1.2 mL) and water (1.2 mL) under an argon atmosphere was added titanium trichloride (0.3 g, 2 mmol). After stirring for 1.5 h at room temperature, titanium trichloride (0.3g, 2 mmol) and water (1.2 mL) were added, and the mixture was stirred for 0.5 h at room temperature and for 0.5 h at 45°–50°C., then was cooled to room temperature. Water (1.2 mL) and ammonium hydroxide (2.5 mL) were added. After stiinng an additional 1 h, methanol (17.5 mL), 5% sodium carbonate (17.5 mL) and dichloromethane (35 mL) were added, and stirring was continued for 2 h. The suspension was filtered through Celite®, was washed well with dichloromethane and the extract was evaporated. The residue was diluted with dichloromethane, the organic layer was washed with 5:95 ammonium hydroxide:water, was dried (potassium carbonate) and was evaporated. Purification by flash chromatography, eluting with 3:7 ethyl acetate:hexanes, provided a mixture of 4-(3-cyclopentyloxy-4-methoxyphenyl)-4-(3-anminophenylethynyl)-cyclohexan-1-one and 4-(3-cyclopentyloxy-4-methoxyphenyl)-1,1-(ethylenedioxy)-4-(3-aminophenylethynyl)cyclohexane (0.07 g). This mixture and a spatula-tip of pyridinium p-toluenesulfonate in acetone (4 mL) and water (1 mL) was refluxed for 3 days, then was evaporated. Water was added, the mixture was extracted three times with dichloromethane, the extract was dried (magnesium sulfate) and was evaporated. Purification by flash chromatography, eluting with 35:65 ethyl acetate:hexanes provided 4-(3-cyclopentyloxy-4-methoxyphenyl)-4-(3-aminophenylethynyl)cyclohexan-1-one as a colorless oil. $^1$H-NMR (400 MHz, CDCl$_3$) δ 7.22 (d, J=2.2 Hz, 1H), 7.14 (m, 2H), 6.87 (m, 2H), 6.82 (d, J=2.8 Hz, 1H), 6.66 (dd, J=9.0, 2.4 Hz, 1H), 4.81 m, 1H), 3.85 (s, 3H), 3.7 (br, 2H), 3.04 (dt, J=14.3, 6.0 Hz, 2H), 2.47 (br d, J=14.6 Hz, 2H), 2.2–2.3 (m, 4), 1.8–2.0 (m, 6H), 1.61 (m, 2H).

EXAMPLE 10

Preparation of 4-(3-cyclopentyloxy-4-methoxyphenyl)-4-(3-acetamidophenylethynyl)cyclohexan-1-one To 4-(3-cyclopentyloxy-4-methoxyphenyl)-4-(3-aminophenylethynyl)cyclohexan-1-one (0.07 g, 0.18 mmol) in dichloromethane (2 mL) under an argon atmosphere. were added pyridine (three drops) and acetic anhydride (0.05 mL, 0.53 mmol) and the reaction was stirred at room temperature for 2 h. Hydrochloric acid (1N) was added, the mixture was extracted three times with dichloromethane, the extract was dried (magnesium sulfate) and was evaporated. Purification by flash chromatography, eluting with 45:55 ethyl acetate:hexanes, provided 4-(3-cyclopentyloxy-4-methoxyphenyl)-4-(3-acetamidophenylethynyl)cyclohexanone as a white solid. mp 63°–64° C.; Anal. ($C_{28}H_{31}NO_4$·1.75 $H_2O$) calcd: C, 70.49; H, 7.29; N, 2.94; found: C, 70.09; H, 6.94; N, 2.83.

EXAMPLE 11

Preparation of 4-(3-cyclopentyloxy-4-methoxyphenyl)-1,1-(ethylenedioxy)-4-(3-carbomethoxyphenylethynyl)cyclohexane A mixture of 4-(3-cyclopentyloxy-4-methoxyphenyl)-1,1-(ethylenedioxy)-4-ethynylcyclohexane (0.150 g, 0.421 mmol) and methyl 3-iodobenzoate (0.110 g, 0.421 mmol) in piperidine (2.1 mL, dry) under an argon atmosphere was treated with a mixture of tetrakis(triphenylphosphine)palladium(0) (0.020 g, 0.017 mmol), cuprous iodide (0.010 g, 0.053 mmol) and triphenylphosphine (crystal) and the mixture was heated at 80° C. for 40 min. The reaction mixture was chilled to 0° C., was poured into ice-water, was acidified with 3N hydrochloric acid and was extracted five times with methylene chloride. The organic phase was washed with dilute hydrochloric acid, water, saturated brine, was dried over magnesium sulfate, was filtered and concentrated in vacuo. The residue was preadsorbed and chromatographed on silica gel, eluting the with 15 to 20% ethyl acetate in hexanes, to afford a light yellow oil. $^1$H-NMR (250 MHz, CDCl$_3$) δ 8.11 (t, J=1.4 Hz, 1H), 7.97 (d-d, J=1.3 Hz;J=7.9 Hz, 1H), 7.63 (d-d, J=7.8 Hz;J=1.3 Hz, 1H), 7.39 (t, J=7.8 Hz, 1H), 7.23 (d, J=2.2, 1H), 7.15 (d-d, J=8.4 Hz;J=2.3 Hz, 1H), 6.89 (d, J=8.4 Hz, 1H), 4.80 (m, 1H), 4.00 (s, br, 4H), 3.92 (s, 3H), 3.84 (s, 3H), 2.4 to 1.75 (m, 18H).

EXAMPLE 12

Preparation of 4-(3-cyclopentyloxy-4-methoxyphenyl)-4-(3-carbomethoxyphenylethynyl)cyclohexan-1-one A solution of 4-(3-cyclopentyloxy-4-methoxyphenyl)-1,1-(ethylenedioxy)-4-(3-carbomethoxyphenylethynyl)cyclohexane (0.060 g, 0.12 mmol) in tetrahydrofuran (5 mL) containing 3N hydrochloric acid (0.60 mL) under an argon atmosphere was heated at 55°–60° C. for 2 h. The cooled reaction mixture was partitioned between ice cold dilute aqueous sodium carbonate solution and ethyl acetate. The organic phase was washed with water, saturated brine, was dried over sodium sulfate, and was concentrated in vacuo. The residue was chromatographed (silica gel), eluting with 15% ethyl acetate/hexanes, to afford a resin. Anal. ($C_{28}H_{30}O_5$·1/4 $H_2O$) calcd: C 74.56, H 6.82, found: C 74.43, H 6.80. $^1$H-NMR (400 MHz, CDCl$_3$) δ 8.15 (s, 1H), 8.00 (d-d, J=1.5 Hz;J=6.6 Hz, 1H), 7.65 (d-d, J=1.3 Hz, J=7.7 Hz, 1H), 7.43 (t, J=7.7 Hz, 1H), 7.21 (d, J=2.1, 1H), 7.12 (d-d, J=2.0 Hz, J=8.5 Hz, 1H), 6.87 (d, J=8.5 Hz,1H), 4.81 (m, 1H), 3.94 (s, 3H), 3.86 (s, 3H), 3.04 (d-t, J=6.0 Hz, J=14.2, 2H), 2.50 (d,br, J=14.8, 2H), 2.4–2.2 (m, 4H), 2.0–1.5 (m).

EXAMPLE 13

Preparation of 4-(3-cyclopentyloxy-4-methoxyphenyl)-1,1-(ethylenedioxy-4-(3-carboxyphenylethynyl)cyclohexane A solution of 4-(3-cyclopentyloxyfmethoxyphenyl)-1,1-(ethylenedioxy)-4-(3-carbomethoxyphenylethynyl)cyclohexane (0.12 g, 0.245 mmol) in methanol (5 mL) was treated with 10% aqueous sodium hydroxide (0.3 mL, 0.734 mmol) under an argon atmosphere and was heated at 55°–60° C. for 2.5 h. The cooled reaction mixture was concentrated in an argon stream and the residue was partitioned between cold water acidified with dilute hydrochloric acid and methylene chloride. The aqueous phase was extracted another two times with methylene chloride and the combined organic phase was dried over magnesium sulfate to afford the titled compound as an oil. $^1$H-NMR (400 Mz, CDCl$_3$) δ 8.18 (s, 1H), 8.02 (d, J=7.9 Hz, 1H), 7.68 (d, J=7.8 Hz,1H), 7.42 (t, J=7.8 Hz, 1H), 7.23 (d, J=2.2, 1H), 7.14 (d-d, J=8.4 Hz;J=2.3 Hz, 1H), 6.85 (d, J=8.4 Hz, 1H), 4.82 (p, 1H), 4.01 (t, 4.2H), 3.85 (s, 3.2H), 2.4 to 1.5 (m, 17H).

EXAMPLE 14

Preparation of 4-(3-cyclopentyloxy-4-methoxyphenyl)-4-(3-carboxyphenylethynyl)cyclohexane-1-one A solution of 4-(3-cyclopentyloxy-4-methoxyphenyl)-1,1-(ethylenedioxy)-4-(3-carboxyphenylethynyl)cyclohexane (0.11 g, 0.23 mmol) in tetrahydrofuran (6 mL) containing 3N hydrochloric acid (0.7 mL) was heated under an argon atmosphere at 55°–70° C. for 2 h. The cooled reaction mixture was concentrated in vacuo and the residue was partitioned between cold water and methylene chloride. The organic phase was washed with saturated brine solution, was dried over magnesium sulfate and was evaporated. The residue was chromatographed (silica), eluting with methylene chloride/methanol/water (90/5/0.25 to 90/10/0.5) and was concentrated in vacuo. The residue was dissolved in methanol and was foamed in vacua to afford a white fractured glass. Anal. (C$_{27}$H$_{28}$O$_5$.1/4 H$_2$O.1/4 CH$_3$OH) calcd: C 73.55, H 6.68, found: C 73.51, H 6.66. $^1$H-NMR (400 MHz, CDCl$_3$) δ 8.22 (t, J=1.5 Hz, 1H), 8.09 (d-d, J=1.3 Hz;J=7.9 Hz, 1H), 7.72 (d-d, J=1.3 Hz, J=7.8 Hz, 1H), 7.47 (t, J=7.8 Hz, 1H), 7.22 (d, J=2.2, 1H), 7.13 (d-d, J=2.3 Hz, J=8.4 Hz, 1H), 6.88 (d, J=8.5 Hz,1H), 4.82 (p, 1H), 3.86 (s, 3H), 3.25 (d, J=20 Hz, CH$_3$OH, 0.55H), 3.04 (d-t, J=5.8 Hz, J=14.5, 1.7H), 2.50 (d,br, J=14.8, 1.8H), 2.4–2.2 (m, 4H), 2.0–1.5 (m).

EXAMPLE 15

4-(3-Cycloeniyloxy-4-methoxyphenyl)-4-(4-pyridylethynyl)cyclohexan-1-one 15a) 4-(3-cyclopentyloxy-4-methoxyphenyl)-4-(4-pyridylethynyl)-1,1-(ethylenedioxy)cyclohexane To a solution of 4-(3-cyclopentyloxy-4-methoxyphenyl)-4-ethynyl-1,1-(ethylenedioxy)cyclohexane (0.10 g, 0.28 mmol) and 4-bromopyridine (0.54 g, 2.8 mmol) in piperidine (1.5 mL) under an argon atmosphere were added tetrakis(triphenyl-phosphine)palladium(0) (0.013 g, 4%), copper(I) iodide (0.004 g, 6%) and a small crystal of triphenylphosphine, and the mixture was heated at 80°–85° C. for 0.5 h. Water was added, the mixture was extracted three times with dichloromethane, was dried (magnesium sulfate),and was evaporated. Purification by flash chromatography, eluting with 35:65 ethyl acetate:hexanes, provided 4-(3-cyclopentyloxy-4-methoxyphenyl)-4-(4-pyridylethynyl)-1,1-(ethylenedioxy)cyclohexane as a pale yellow oil (0.11 g, 93%). $^1$H-NMR (400 MHz, CDCl$_3$) δ 8.56 (d, J=5.3 Hz, 2H), 7.33 (d, J=5.3 Hz, 2H), 7.16 (d, J=2.2 Hz, 1H), 7.09 (dd, J=8.5, 2.2 Hz, 1H), 6.85 (d, J=8.5 Hz, 1H), 4.80 (m, 1H), 4.00 (m, 4H), 3.85 (s, 3H), 2.0–2.2 (m, 6H), 1.8–2.0 (m, 8H), 1.59 (m, 2H).

15b) 4-(3-cyclopentyloxy-4-medioxyphenyl)-4-(4-pyrdylethynyl)cyclohexan-1-one

A mixture of 4-(3-cyclopentyloxy-4-methoxyphenyl)-4-(4-pyridylethynyl)-1,1-(ethylenedioxy)cyclohexane (0.10 g, 0.24 mmol) and pyridinium p-toluenesulfonate (0.06 g, 0.24 mmol) in acetone (4 mL) and water (1 mL) was refluxed for 20 h., then was evaporated. Water was added, the mixture was extracted three times with dichloromethane, was dried (magnesium sulfate) and was evaporated. Purification by flash chromatography, eluting with 35:65 ethyl acetate:hexanes, provided 4-(3-cyclopentyloxy-4-methoxyphenyl)-4-(4-pyridylethynyl)cyclohexan-1-one (0.08 g, 91%) as a white solid, mp 148°–149° C. Anal. (C$_{25}$H$_{27}$NO$_3$.0.5 H$_2$O) calcd: C, 75.29; H, 7.08; N, 3.51; found: C, 75.51; H, 6.95; N, 3.42.

EXAMPLE 16

4-(3-Cyclopentyloxy-4-methoxyphenyl)-4-(3-pyridylethynyl)cyclohexan-1-one

To a solution of 4-(3-cyclopentyloxy-4-methoxyphenyl)-4-ethynylcyclohexan-1-one (0.22 g, 0.70 mmol) and 3-bromopyridine (0.70 mL, 7.0 mmol) in piperidine (2 mL) under an argon atmosphere were added tetakis(triphenylphosphine)palladium(0) (0.034 g, 4%), copper(I) iodide (0.009 g, 6%) and a small crystal of triphenylphosphine, and the mixture was heated at 80°–85° C. for 0.5 h. Ammonium chloride was added, the mixture was extracted three times with dichloromethane, was dried (magnesium sulfate) and was evaporated. Purification by flash chromatography, eluting with 35:65 ethyl acetate:hexanes, provided 4-(3-cyclopentyloxy-4-methoxyphenyl)-4-(4-pyridylethynyl)cyclohexan-1-one as an off-white solid (0.22 g, 80%). The product was further triturated from ether-hexanes, mp 88°–89° C. Anal. (C$_{25}$H$_{27}$NO$_3$.0.375 H$_2$O) calcd: C, 75.78; H, 7.03; N, 3.53; found: C, 75.77; H, 6.89; N, 3.40.

EXAMPLE 17

4-(2-Carbomethoxythien-5-ylethynyl)-4-(3-cyclopentyloxy-4-methoxyphenyl)cyclohexan-1-one 17a) 2-bromo-5-carboxymethylthiophene 2-Bromo-5-carboxymetiylthiophene was prepared by standard chemistry well known to those versed in the art and was a white solid, mp 59°–60° C.

17b) 4-(2-carboiethoxythien-5-ylethynyl)-4-(3-cyclopentyloxy-4-methoxyphenyl)cyclohexan-1-one To a solution of 4-(3-cyclopentyloxy-4-methoxyphenyl)-4-ethynylcyclohexan-1-one (0.21 g, 0.7 mmol) and 2-bromo-5-carboxymethylthiophene (0.18 g, 1.2 mmol) in triethylamine (2 mL) under an argon atmosphere were added tetrakis(triphenylphosphine)palladium(0) (0.031 g, 4%), and copper(I) iodide (0.008 g, 6%), and the mixture was heated at 80°–85° C. for 4.5 h. Ammonium chloride was added and the mixture was extracted three times with dichloromethane, was dried (magnesium sulfate),and was evaporated. Purification by flash chromatography, eluting with 2:8 ethyl acetate:hexanes, provided 4-(2-carbomethoxythien-5-ylethynyl)-4-(3-cyclopentyloxy-4-methoxyphenyl)cyclohexan-1-one as a yellow oil (0.25 g, 82%). $^1$H-NMR (400 MHz, CDCl$_3$) δ 7.67 (d, J=4.0 Hz, 1H), 7.16 (d, J=4.0 Hz, 1H), 7.15 (d, J=2.2 Hz, 1H), 7.07 (dd, J=8.4, 2.2 Hz, 1H), 6.87 (d, J=8.4 Hz, 1H), 4.80 (m, 1H), 3.89 (s, 3H), 3.85 (s, 3H), 2.95 (dt, J=14.5, 5.9 Hz, 2H), 2.49 (br d, J=14.5 Hz, 2H), 2.36 (m, 2H), 2.26 (dt, J=13.4, 4.0 Hz, 2H), 1.8–2.0 (m, 6H), 1.6 (m, 2H) ppm. Anal. (C$_{26}$H$_{28}$O$_5$S.0.25 H$_2$O) calcd: C, 68.32; H, 6.28; found: C, 68.25 H, 6.12.

EXAMPLE 18

4-(2-Carboxythien-5-ylethynyl)-4-(3-cyclopentyloxy-4-methoxyphenyl)cyclohexan-1-one, sodium salt A solution of 4-(2-carbomethoxythien-5-ylethynyl)-4-(3-cyclopentyloxy-4-methoxyphenyl)cyclohexan-1-one (0.13 g, 0.30 mmol) and coarsely ground potassium hydroxide (0.025 g, 0.45 mmol) in tetrahydrofuran (5 mL), methanol (5 mL), and water (2 mL) was stirred at room temperature under an argon atmosphere for 24 h. The reaction was acidified (10% HCl), was extracted three times with 5:95 methanol:dichloromethane, was dried (magnesium sulfate) and was evaporated. The crude product was treated with 10% sodium hydroxide to form the salt. Reverse phase chromatography, eluting with 1:1 methanol:water, provided 4-(2-carboxythien-5-ylethynyl)-(3-cyclopentyloxy-4-methoxyphenyl)cyclohexan-1-one, sodium salt, as a white solid (0.070 g, 55%), mp 194°–195° C. Anal. ($C_{25}H_{25}O_5SNa.1.25 H_2O$) calcd: C, 62.16; H, 5.74; found: C, 61.90; H, 5.49.

EXAMPLE 19

4-(2-Cyanothien-5-ylethynyl)-4-(3-cyclopentyloxy-4-methoxyphenyl)cyclohexan-1-one 19a) 2-bromo-5-cyanothiophene 2-Bromo-5-cyanothiophene was prepared by standard chemistry well known to those versed in the art and was a colorless oil, $^1$H-NMR (400 MHz, $CDCl_3$): δ 7.40 (d, J=4 Hz, 1H), 7.10 (d, J=4 Hz, 1H) ppm.

19b) 4-(2-cyanothien-5-ylethynyl)-4-(3-cyclopentyloxy-4-methoxyphenyl)cyclohexan-1-one To a solution of 4-(3-cyclopentyloxy-4-methoxyphenyl)-4-ethynyl-cyclohexan-1-one (0.22 g, 0.7 mmol) and 2-bromo-5-cyanothiophene (0.13 g, 0.7 mmol) in triethylamine (5 mL) under an argon atmosphere were added tetrakis(triphenylphosphine)palladium(0) (0.034 g, 4%) and copper(I) iodide (0.007 g, 6%), and the mixture was heated at 85°–90° C. for 2 h. Ammonium chloride was added and the mixture was extracted three times with dichloromethane, was dried (magnesium sulfate) and was evaporated. Purification by flash chromatography, eluting with 2:8 ethyl acetate:hexanes, provided 4-(2-cyanothien-5-ylethynyl)-4-(3-cyclopentyloxy-4-methoxyphenyl)cyclohexan-1-one (0.06 g, 18%). This was combined with product (0.017 g) obtained in a second, similar reaction and was triturated from dichloromethane-hexanes to provide a white solid, mp 106°–107° C. Anal. ($C_{25}H_{25}NO_3S.0.5 H_2O$) calcd: C, 70.07; H, 6.11; N, 3.27; found: C, 70.15; H, 5.84; N, 3.32.

EXAMPLE 20

4-(3-Cyclopentyloxy-4-methoxyphenyl)-4-[5-(5-methyl-[1,2,4]oxadiazol-2-yl)thien-2-ylethynyl]cyclohexan-1-one 20a) 2-bromo-5-(5-methyl-[1,2,4]oxadiazol-2-yl)thiophene 2-Bromo-5-(5-methyl-[1,2,4]oxadiazol-2-yl)thiophene was prepared by standard chemistry well known to those versed in the art and was a white solid, mp 48°–49° C.

20b) 4-(3-cyclopentyloxy-4-methoxyphenyl)-4-[5-(5-methyl-[1,2,4]oxadiazol-2-yl)thien-2-ylethynyl]cyclohexan-1-one To a solution of 4-(3-cyclopentyloxy-4-methoxyphenyl)-4-ethynyl-cyclohexan-1-one (0.17 g, 0.88 mmol) and 2-bromo-5-(5-methyl-[1,2,4]oxadiazol-2-yl)thiophene (0.18 g, 1.2 mmol) in triethylamine (5 mL) under an argon atmosphere were added tetrakis(triphenylphosphine)palladium(0) (0.037 g, 4%) and copper(I) iodide (0.010 g, 6%), and the mixture was heated at 85°–90° C. for 2 h. Ammonium chloride was added and the mixture was extracted three times with dichloromethane, was dried (magnesium sulfate) and was evaporated. Purification by flash chromatography, eluting with 25:75 ethyl acetate:hexanes, provided 4-(3-cyclopentyloxy-4-methoxyphenyl)-4-[5-(5-methyl-[1,2,4]oxadiazol-2-yl)thien-2-ylethynyl]cyclohexan-1-one as a white wax (0.17 g, 45%), mp 94°–95° C. Anal. ($C_{27}H_{28}N_2O_4S$) calcd: C, 68.04; H, 5.92; N, 5.88; found: C, 67.83; H, 5.89; N, 5.92.

EXAMPLE 21

4-(2-Carbomethoxythien-4-ylethynyl)-4-(3-cyclopentyloxy-4-methoxyphenyl)cyclohexan-1-one 21a) 4-bromo-2-carboxymethylthiophene 4-Bromo-2-carboxymethylthiophene was prepared by standard chemistry well known to those versed in the art and was a brown oil. $^1$H-NMR (400 MHz, $CDCl_3$) δ 7.69 (d, J=1.5 Hz, 1H), 7.45 (d, J=1.5 Hz, 1H), 3.90 (s, 3H) ppm.

21b) 4-(2-methoxythien-4-ylethynyl)-4-(3-cyclopentyloxy-4-methoxyphenyl)cyclo-hexan-1-one.

To a solution of 4-(3-cyclopentyloxy-4-methoxyphenyl)-4-ethynylcyclohexan-1-one (0.25 g, 0.8 mmol) and 4-bromo-2-carboxymethylthiophene (0.27 g, 1.2 mmol) in triethylamine (3.5 mL) under an argon atmosphere were added tetrakis(triphenylphosphine)palladium(0) (0.038 g, 4%) and copper(I) iodide (0.010 g, 6%), and the mixture was heated at 80°–85° C. for 0.5 h. Ammonium chloride was added and the mixture was extracted three times with dichloromethane, was dried (magnesium sulfate) and was evaporated. Purification by flash chromatography, eluting with 2:8 ethyl acetate:hexanes, provided 4-(2-carbomethoxythien-4-ylethynyl)-4-(3-cyclopentyloxy-4-methoxyphenyl)cyclohexan-1-one as a yellow glass (0.15 g, 42%). $^1$H-NMR (400 MHz, $CDCl_3$) δ 7.81 (d, J=1.3 Hz, 1H), 7.60 (d, J=1.3 Hz, 1H), 7.16 (d, J=2.2 Hz, 1H), 7.10 (dd, J=8.5, 2.2 Hz, 1H), 6.86 (d, J=8.5 Hz, 1H), 4.80 (m, 1H), 3.90 (s, 3H), 3.84 (s, 3H), 2.98 (dt, J=14.8, 5.7 Hz, 2H), 2.48 (br d, J=14.8 Hz, 2H), 3.33 (m, 2H), 2.26 (dt, J=13.6, 4 Hz, 2H), 1.9–2.0 (m, 6H), 1.6 (m, 2H) ppm. Anal. ($C_{26}H_{28}O_5S$) calcd: C, 69.00; H, 6.24; found: C, 68.82; H, 6.04.

EXAMPLE 22

4-(2-Carboxythien-4-ylethynyl)-4-(3-cyclopentyloxy-4-methoxyphenyl)cyclohexan-1-one A solution of 4-(2-carbomethoxythien-4-ylethynyl)-4-(3-cyclopentyloxy-4-methoxyphenyl)cyclohexan-1-one (0.19 g, 0.43 mmol) and coarsely ground potassium hydroxide (0.036 g, 0.64 mmol) in tetrahydrofuran (2 mL), methanol (2 mL), and water (0.4 mL) was stirred at room temperature under an argon atmosphere for 24 h. The reaction was acidified (10% HCl), was extracted three times with 5:95 methanol:dichloromethane, was dried (magnesium sulfate) and was evaporated. Purification by flash chromatography, eluting with 0.1:3:97 acetic acid:methanol:dichloromethane, provided 4-(2-carboxythien-4-ylethynyl)-4-(3-cyclopentyloxy-4-methoxyphenyl)cyclohexan-1-one as an off-white solid (0.18 g, 95%), mp 80°–82° C. Anal. ($C_{25}H_{26}O_5S.0.25 H_2O$) calcd: C, 67.78; H, 6.03; found: C, 67.72; H, 6.02.

EXAMPLE 23

4-(2-Cyanothien-4-ylethyl)-4-(3-cyclontyloxy-4-methoxyphenyl)cyclohexan-1-one 23a) 4-bromo-2-cyanothiophene 4-Bromo-2-cyanothiophene was prepared by standard chemistry well known to those versed in the art and was a pinkish solid, mp 43°–44° C.

23b) 4-(2-cyanothien-4-ylethynyl)-4-(3-cyclopentyloxy-4-methoxyphenyl)cyclohexan-1-one.

To a solution of 4-(3-cyclopentyloxy-4-methoxyphenyl)-4-ethynylcyclohexan-1-one (0.25 g, 0.8 mmol) and 4-bromo-2-cyanothiophene (0.15 g, 0.8 mmol) in triethylamine (5 mL) under an argon atmosphere were added tetrakis(triphenylphosphine)palladium(0) (0.038 g, 4%) and copper(I) iodide (0.008 g, 6%), and the mixture was heated at 85°–90° C. for 24 h. Water was added and the mixture was extracted three times with dichloromethane, was dried (magnesium sulfate) and was evaporatei Purification by flash chromatography, eluting with 2:8 ethyl acetate:hexanes, provided 4-(2-cyanothienfylethynyl)-4-(3-cyclopentyloxy-4-methoxyphenyl)cyclohexan-1-one, which was further triturated from dichloromethanehexanes as a white solid (0.08 g, 24%), mp 112°–113° C. Anal. ($C_{25}H_{25}NO_3S \cdot 0.375\ H_2O$) calcd: C, 70.44; H, 6.09; N, 3.29; found: C, 70.38; H, 5.94; N, 3.20.

EXAMPLE 24

4-(3-Cyclopentyloxy-4-methoxyphenyl)-4-[2-(5-methyl-[1,2,4]oxadiazol-2-yl)thien-4-ylethynyl]cyclohexan-1-one 24a) 4-bromo-2-(5-methyl-[1,2,4]oxadiazol-2-yl)thiophene 4-Bromo-2-(5-methyl-[1,2,4]oxadiazol-2-yl)thiophene was prepared by standard chemistry well known to those versed in the art and is a white solid, mp 66°–67° C.

24-b) cis-[4-(3-cyclopentyloxy-4-methoxyphenyl)-4-[2-(5-methyl-[1,2,4]oxadiazol-2-yl)thien-4-ylethynyl]cyclohexan-1-ol]

To a solution of trans-[4-(3-cyclopentyloxy-4-methoxyphenyl)-4-ethynylcyclohexan-1-ol] (0.25 g, 0.8 mmol, prepared as described in a co-pending application identified as P50287 and filed on even day herewith) and 4-bromo-2-(5-methyl-[1,2,4]oxadiazol-2-yl)thiophene (0.20 g, 0.8 mmol) in triethylamine (5 mL) under an argon atmosphere were added tetrakis(triphenylphosphine)palladium(0) (0.038 g, 4%), copper(I) iodide (0.009 g, 6%), and a small crystal of triphenylphosphine, and the mixture was heated at 70°–75° C. for 0.5 h. Hydrochloric acid (5%) was added and the mixture was extracted three times with dichloromethane, was dried (magnesium sulfate) and was evaporated. Purification by flash chromatography, eluting with 1:1 ethyl acetate:hexanes, provided cis-[4-(3-cyclopentyloxy-4-methoxyphenyl)-4-[2-(5-methyl-[1,2,4]oxadiazol-2-yl)thien-4-ylethynyl] cyclohexan-1-ol] (0.20 g, 53%), which was further triturated from dichloromethane-hexanes to give a white solid, mp 142°–143° C. Anal. ($C_{27}H_{30}N_2O_4S$) calcd: C, 67.76; H, 6.32; N, 5.85; found: C, 67.85; H, 6.42; N, 5.54.

24c) 4-(3-cyclopentyloxy-4-methoxyphenyl)-4-[2-(5-methyl-[1,2,4]oxadiazol-2-yl)thien-4-ylethynyl]cyclohexan-1-one To a suspension of pyridinium chlorochiomate (0.04 g, 0.20 mmol) in dichloromethane (1 mL) at room temperature under an argon atmosphere was rapidly added a solution of cis-[4-(3-cyclopentyloxy-4-methoxyphenyl)-4-[2-(5-methyl-[1,2,4]oxadiazol-2-yl)thien-4-ylethynyl] cyclohexan-1-ol] (0.06 g, 0.13 mmol) in dichloromethane (2 mL) and the mixture was stirred for 1 h. Ether (20 mL) was added and stirring was continued for 0.25 h. The mixture was filtered through Celite® and was evaporated. Purification by flash chromatography, eluting with 25:75 ethyl acetate:hexanes, provided 4-(3-cyclopentyloxy-4-methoxyphenyl)-4-[2-(5-methyl-[1,2,4]oxadiazol-2-yl)thien-4-ylethynyl] cyclohexan-1-one as a colorless oil. Recrystallization from dichloromethane-hexanes provided a white solid (0.033 g, 53%), mp 94°–95° C. Anal. ($C_{27}H_{28}N_2O_4S \cdot 1.0\ H_2O$) calcd: C, 65.57; H, 6.11; N, 5.66; found: C, 65.46; H, 5.74; N, 5.60.

EXAMPLE 25

4-(4-Carbomethoxythien-2ylethynyl)-4-(3-cyclopentyloxy-4-methoxyphenyl)cyclohexan-1-one 25a) 2-bromo-4-carboxymethylthiophene 2-Bromo-4-carboxymethylthiophene was prepared by standard chemistry well known to those versed in the art and is a brown oil. $^1$H-NMR (400 MHz, CDCl$_3$) δ 7.99 (s, 1H), 7.47 (s, 1H), 3.86 (s, 3H) ppm.

25b) 4-(4-carbomethoxythien-2-ylethynyl)-4-(3-cyclopentyloxy-4-methoxyphenyl)cyclohexan-1-one To a solution of 4-(3-cyclopentyloxy-4-methoxyphenyl)-4-ethynyl-cyclohexan-1-one (0.35 g, 1.12 mmol) and 2-bromo-4-carboxymethylthiophene (0.25 g, 1.13 mmol) in triethylamine (5 mL) under an argon atmosphere were added tetrakis(triphenyl-phosphine)palladium(0) (0.044 g, 4%), copper(I) iodide (0.011 g, 6%), and a small crystal of triphenylphosphine, and the mixture was heated at 80°–85° C. for 0.5 h. Water and hydrochloric acid (10%) were added and the mixture was extracted three times with dichloromethane, was dried (magnesium sulfate) and was evaporated. Purification by flash chromatography, eluting with 2:8 ethyl acetate:hexanes, provided 4-(4-carbomethoxythien-2-ylethynyl)-4-(3-cyclopentyloxy-4-methoxyphenyl)cyclohexan-1-one as a yellow gum (0.29 g, 58%). $^1$H-NMR (400 MHz, CDCl$_3$) δ 8.00 (d, J=1.1 Hz, 1H), 7.61 (d, J=1.1 Hz, 1H), 7.16 (d, J=2.2 Hz, 1H), 7.07 (dd, J=8.4, 2.2 Hz, 1H), 6.87 (d, J=8.4 Hz, 1H), 4.81 (m, 1H), 3.88 (s, 3H), 3.86 (s, 3H), 2.97 (dt, J=14.4, 5.7 Hz, 2H), 2.49 (br d, J=13.5 Hz, 2H), 2.35 (m, 2H), 2.29 (m, 2H), 1.9–2.0 (m, 6H), 1.6 (m, 2H) ppm. Anal. ($C_{26}H_{28}O_5S$) calcd: C, 69.00; H, 6.24; found: C, 68.76; H, 6.46.

EXAMPLE 26

4-(4-Carboxythien-2-ylethynyl)-4-(3-cyclopentyloxy-4-methoxyphenyl)cyclohexan-1-one A solution of 4-(4-carbomethoxythien-2-ylethynyl)-4-(3-cyclopentyloxy-4-methoxyphenyl)cyclohexan-1-one (0.12 g, 0.427 mmol) and coarsely ground potassium hydroxide (0.045 g, 0.81 mmol) in tetrahydrofuran (2.5 mL), methanol (2.5 mL), and water (0.5 mL) was stirre at room temperature under an argon atmosphere for three days. The reaction was acidified (10% HCl), was extracted three times with 5:95 methanol:dichloromethane, was dried (magnesium sulfate) and was evaporated. Purification by flash chromatography, eluting with 0.25:2.5:97.5 acetic acid:methanol:dichloromethane, provided 4-(4-carboxythien-2-ylethynyl)-4-(3-cyclopentyloxy-4-methoxyphenyl)cyclohexan-1-one as an off- white foam (0.11 g, 94%), mp 75°–76° C. Anal. ($C_{25}H_{26}O_5S \cdot 0.25\ H_2O$) calcd: C, 67.78; H, 6.03; found: C, 67.73; H, 5.80.

EXAMPLE 27

4-(3-cyclopentyloxy-4-methoxyphenyl)-4-[4-(5-methyl-[1,2,4]oxadiazol-2-yl)thien-2-ylethynyl]cyclohexan-1-one 27a) 2-bromo-4-(5-methyl-[1,2,4]oxadiazol-2-yl)thiophene 2-Bromo-4-(5-methyl-[1,2,4]oxadiazol-2-yl)thiophene was prepared by standard chemistry well known to those versed in the art and was a white solid, mp 72°–73° C.

27b) cis-[4-(3-cyclopentyloxy-4-methoxyphenyl)-4-[4-(5-methyl-[1,2,4]oxadiazol-2-yl)thien-2-ylethynyl]cyclohexan-1-ol]

To a solution of trans-[4-(3-cyclopentyloxy-4-methoxyphenyl)-4-ethynylcyclohexan-1-ol (0.25 g, 0.8 mmol; prepared as described in a co-pending application filed by the same inventors, identified as P50287 and filed on even day herewith) and 2-bromo-4-(5-methyl-[1,2,4] oxadiazol-2-yl)thiophene (0.20 g, 0.8 mmol) in triethylamine (5 mL) under an argon atmosphere were added tetrakis(triphenylphosphine)palladium(0) (0.038 g, 4%), copper(I) iodide (0.009 g, 6%), and a small crystal of triphenylphosphine, and the mixture was heated at 70°–75° C. for 0.5 h. Hydrochloric acid (5%) was added and the mixture was extracted three times with dichloromethane, was dried (magnesium sulfate) and was evaporated. Purification by flash chromatography, eluting with 1:1 ethyl acetate:hexanes provided cis-[4-(3-cyclopentyloxy-4-methoxyphenyl)-4-[4-(5-methyl-[1,2,4]oxadiazol-2-yl) thien-2-ylethynyl] cyclohexan-1-ol], which was further triturated from dichloromethane-hexanes to give a white solid (0.20 g, 53%), mp 142°–143° C. Anal. ($C_{27}H_{30}N_2O_4S.0.75\ H_2O$) calcd: C, 65.90; H. 6.45; N, 5.69; found: C, 66.06; H, 6.42; N, 5.50.

27c) 4-(3-cyclopentyloxy-4-methoxyphenyl)-4-[4-(5-methyl-[1,2,4]oxadiazol-2-yl)thien-2-ylethynyl] cyclohexan-1-one.

To a suspension of pyridinium chlorochromate (0.07 g, 0.31 mmol) in dichloromethane (1 mL) at room temperature under an argon atmosphere was rapidly added a solution of cis-[4-(3-cyclopentyloxy-4-methoxyphenyl)-4-[4-(5-methyl-[1,2,4]oxadiazol-2-yl)thien-2-ylethynyl] cyclohexan-1-ol] (0.10 g, 0.21 mmol) in dichloromethane (2 mL) and stirred 0.5 h. Ether (20 mL) was added and stirring continued for 0.5 h. The mixture was filtered through Celite® and was evaporated. Purification by flash chromatography, eluting with 25:75 ethyl acetate:hexanes, provided 4-(3-cyclopentyloxy-4-methoxyphenyl)-4-[4-(5-methyl-[1,2,4]oxadiazol-2-yl)thien-2-ylethynyl] cyclohexan-1-one as a white solid, mp 90°–91° C. Anal. ($C_{27}H_{28}N_2O_4S.0.25\ H_2O$) calcd: C, 67.41; H, 5.97; N, 5.82; found: C, 67.43; H, 5.87; N, 5.80.

EXAMPLE 28

4-(3-Cyclopentyloxy-4-methoxyphenyl)-4-(2-methylsulfonylpyrimidin-4-ylethynyl) cyclohexan-1-one 28a) 4-iodo-2-thiomethylpyrimidine 4-Iodo-2-thiomethylpyrimidine was prepared following a literature procedure (A.J. Majeed, Ø. Antonsen, T. Benneche, K. Undheim. Tetrahedron 1989, 45, 993–1006).

28b) 4-(3-cyclopentyloxy-4-methoxyphenyl)-4-(2-methylthiopyrimidin-4-ylethynyl) cyclohexan-1-one To a solution of 4-(3-cyclopentyloxy-4-methoxyphenyl)-4-ethynyl-cyclohexan-1-one (0.35 g, 1.12 mmol) and and 4-iodo-2-thiomethylpyrimidine(0.56 g, 2.4 mmol, as a mixture of 4-iodo-2-thiomethylpyrimidine and 4-chloro-2-thiomethylpyrimidine) in triethylamine (5 mL) under an argon atmosphere were added tetrakis(triphenylphosphine) palladium(0) (0.051 g, 4%) and copper(I) iodide (0.014 g, 6%), and the mixture was heated at 85°–90° C. for 0.5 h. Ammonium chloride was added and the mixture was extracted three times with dichloromethane, was dried (magnesium sulfate) and was evaporated. Purification by flash chromatography, eluting with 25:75 ethyl acetate:hexanes, provided 4-(3-cyclopentyloxy-4-methoxyphenyl)-4-(2-methylthiopyrinidin-4-ylethynyl) cyclohexan-1-one as a yellow resin (0.35 g, 72%). $^1$H-NMR (400 MHz, CDCl$_3$) δ 8.50 (d, J=5.3 Hz, 1H), 7.17 (d, J=2.3 Hz, 1H), 7.08 (dd, J=8.5, 2.3 Hz, 1H), 7.03 (d, J=5.3 Hz, 1H), 6.87 (d, J=8.5 Hz, 1H), 4.81 (m, 1H), 3.86 (s, 3H), 2.99 (dt, J=14.7, 8.7 Hz, 2H), 2.58 (s, 3H), 2.46 (br d, J=18.7 Hz, 2H), 2.40 (m, 2H), 2.29 (m, 2H), 1.8–2.0 (m, 6H), 1.6 (m, 2H) ppm.

28c) 4-(3-cyclopentyloxy-4-methoxyphenyl)-4-(2-methylsulfonylpyrimidin-4-ylethynyl)cyclohexan-1-one To a solution of 4-(3-cyclopentyloxy-4-methoxyphenyl)-4-(2-methylthiopyrimidin-4-ylethynyl)cyclohexan-1-one (0.35 g, 0.81 mmol) in chloroform (5 mL) at –10° C. under an argon atmosphere was dropwise added over 20 min a solution of 3-chloroperoxybenzoic acid (0.31 g, 1.78 mmol) in chloroform. The reaction was stired for 1 h at –10° C., then for 1 h at room temperature, then was treated with 5% sodium carbonate, was extracted three times with dichloromethane, was dried (potassium carbonate) and was evaporated. Purification by flash chromatography, eluting with 1:99 methanol:dichloromethane, provided 4-(3-cyclopentyloxy-4-methoxyphenyl)-4-(2-methylsulfonylpyrimidin-4-ylethynyl)cyclohexan-1-one as a white foam (0.27 g, 72%), mp 60°–64° C. A second batch was provided by oxidation of the sulfoxide as a white foam, mp 71°–73° C. Anal. ($C_{25}H_{28}N_2O_5S.0.25\ H_2O$) calcd: C, 63.47; H, 6.07; N, 5.92; found: C, 63.43; H, 6.07; N, 5.58.

EXAMPLE 29

4-(2-Aminopyrimidin-4-ylethynyl-4-(3-cyclopentyloxy-4-methoxyphenyl)cyclohexan-1-one Into a solution of 4-(3-cyclopentyloxy-4-methoxyphenyl)-4-(2-methylsulfonylpyrimidin-4-ylethynyl)cyclohexan-1-one (0.26 g, 0.56 mmol) in methanol (4 mL) at –78° C. was condensed liquid ammonia (4 mL), the pressure tube was sealed and the reaction was stirred at room temperature for 2.5 h. After cooling, the solvents were evaporated. Purification required two flash chromatographies, eluting first with 2:98 methanol:dichloromethane and secondly with 4:6 ethyl acetate:hexanes, to provide 4-(2-aminopyrimidin-4-ylethynyl)-4-(3-cyclopentyloxy-4-methoxyphenyl) cyclohexan-1-one as a white solid (0.18 g, 73%), mp 68°–70° C. Anal. ($C_{24}H_{27}N_3O_3.0.2\ H_2O$) calcd: C, 70.46; H, 6.75; N, 10.27; found: C, 70.73; H, 6.79; N, 9.87.

EXAMPLE 30

4-(3-cyclopentyloxy-4-methoxyphenyl)-4-(1-methylimidazol-2-ylethynyl)cyclohexan-1-one 30a) 1-methyl-2-iodoimidazole 1-Methyl-2-iodoimidazole was prepared by standard chemistry well known to those versed in the art and was a white solid, mp 58°–59° C.

30b) 4-(3-cyclopentyloxy-4-methoxyphenyl)-4-(1-methylimidazol-2-ylethynyl) cyclohexan-1-one To a solution of 4-(3-cyclopentyloxy-4-methoxyphenyl)-4-ethynylcyclohexan-1-one (0.50 g, 1.6 mmol) and 1-methyl-2-iodoimidazole (0.35 g, 1.6 mmol) in triethylamine (50 mL) under an argon atmosphere were added tetrakis(triphenylphosphine)palladium(0) (0.074 g, 4%), copper(I) iodide (0.018 g, 6%), and a small crystal of triphenylphosphine, and the mixture was heated at 80°–85° C. for 1 h. Water was added and the mixture was extracted three times with dichloromethane, was dried (magnesium sulfate) and was evaporated. Purification by flash chromatography, eluting with 3:1 ethyl acetate:hexanes, provided impure 4-(4-carbomethoxythien-2-ylethynyl)-4-(3-yclopentyloxy-4-methoxyphenyl)cyclohexan-1-one (0.16 g, 26%), which was combined with product from a second reaction (0.16 g, 43%) and purified by flash chromatography, eluting with 1:99 methanol:dichloromethane, followed by recrystallization from dichloromethanehexanes, to provide pure 4-(3-cyclopentyloxy-4-methoxyphenyl)-4-(1-methylimidazol-2- ylethynyl)cyclohexan-1-one (0.12 g) as an off-white solid, mp 137°–138° C. Anal. ($C_{24}H_{28}N_2O_3 \cdot 0.2\ H_2O$) calcd: C, 72.77; H, 7.23; N, 7.07; found: C, 72.82; H, 7.99; N, 6.97.

EXAMPLE 31

4-(3-cyclopentyloxy-4-methoxyphenyl)-4-(imidazol-2-ylethynyl)cyclohexan-1-one, hydrochloride salt 31 a) 1-tert-butylcarbonyl-2-iodoimidazole 1-tert-Butylcarbonyl-2-iodoimidazole was prepared by standard chemistry well known to those versed in the art and was a white solid, mp 77°–78° C.

31b) 4-(3-cyclopentyloxy-4-methoxyphenyl)-4-(1-tert-butylcarboxyimidazol-2-ylethynyl) cyclohexan-1-one To a solution of 4-(3-cyclopentyloxy-4-methoxyphenyl)-4-ethynylcyclohexan-1-one (0.28g, 0.9 mmol) and 1-tert.-butylcarbonyl-2-iodoimidazole (0.29 g, 0.97 mmol) in triethylamine (5 mL) under an argon atmosphere were added tetrakis(triphenyl-phosphine)palladium(0) (0.042 g, 4%), copper(I) iodide (0.005 g, 6%), and a small crystal of triphenylphosphine, and the mixture was heated at 80°–85° C. for 1 h. Water was added and the mixture was extracted three times with dichloromethane, was dried (magnesium sulfate) and was evaporated. Purification by flash chromatography, eluting with 3:7 ethyl acetate:hexanes provided 4-(3-cyclopentyloxy-4-methoxyphenyl)-4-(1-tert-butylcarbonylimidazol-2-ylethynyl)cyclohexan-1-one (0.18 g, 4%), as a colorless oil. 1H-NMR (400 MHz, $CDCl_3$) δ 7.36 (s, 1H), 7.20 (d, J=2.1 Hz, 1H), 7.17 (dd, J=8.5, 2.1 Hz, 1H), 7.01 (s, 1H), 6.85 (d, J=8.5 Hz, 1H), 4.85 (m, 1H), 3.84 (s, 3H), 3.18 (m, 2H), 2.44 (m, 4H), 2.22 (m, 2H), 1.8–2.0 (m, 6H), 1.6 (m, 11H) ppm.

31c) 4-(3-cyclopentyloxy-4-methoxyphenyl)-4-(imidazol-2-ylethynyl)cyclohexan-1-one, hydrochloride salt A solution of 4-(3-cyclopentyloxy-4-methoxyphenyl)-4-(1-tert-butylcarbonylimidazol-2-ylethynyl)cyclohexan-1-one (0.18 g, 0.37 mmol) and hydrogen chloride-saturated ethyl acetate (40 drops) in ethyl acetate (10 mL) was stirred under an argon atmosphere at room temperature for 24 h. The suspension was cooled to 0° C. and filtered to provide 4-(3-cyclopentyloxy-4-methoxyphenyl)-4-(imidazol-2-ylethynyl)-cyclohexan-1-one, hydrochloride salt (0.12 g, 76%) as a white solid, mp 183°–184° C. Anal. ($C_{23}H_{26}N_2O_3 \cdot HCl \cdot 0.25\ H_2O$) calcd: C, 65.70; H, 6.83; N, 6.66; found: C, 65.46; H, 6.65; N, 6.44.

EXAMPLE 32

Preparation of 4-(3-cyclopentyloxy-4-methoxyphenyl)-4-(2-[4-(2-hydroxyethan-1-oxy)phenyl]ethynyl)cyclohexan-1-one 32a) 4-(2-hydroxyethoxy)phenyl iodide A melt of ethylene carbonate (6.5 g, 74 mmol) in a small flask under Argon was treated with 4-iodophenol (0.400 g, 1.82 mmol) and powdered potassium carbonate (1.26 g, 9.1 mmol) and was stirred at 90° C. for 3 hr. The mixture was treated with cold dilute hydrochloric acid to decompose the excess potassium carbonate and excess aqueous sodium hydroxide solution was slowly added and the mixture was stirred over night. The suspension was extracted with methylene chloride, was washed with water and brine, was dried over sodium sulfate and was stripped to afford a white solid, which was purified by flash chromatography on silica gel (20 mL) with methylene chloride to afford (0.128 g, 27%) of the titled intermediate as a white solid, mp 76°–77.5° C.

32b) 4-(3-cyclopentyloxy-4-methoxyphenyl)-4-(2-[4-(2-hydroxyethan-1-oxy)phenyl]ethynyl)-1,1-(ethylenedioxy) cyclohexane A solution of 4-(2-hydroxyethoxy)phenyl iodide (0.059 g, 0.22 mmol), and 4-(3-cyclopentyloxy-4-methoxyphenyl)-1,1-(ethylenedioxy)-4-ethynylcyclohexane (0.080 g, 0.22 nmol) in dry piperidine (1 mL) was treated with a mixture of tetrakis(triphenylphosphine)palladium (0.013 g, 0.011 mmol), cuprous iodide (0.0025 g, 0.013 mmol), and triphenylphosphine (crystal), as described above in Example 11. Purification of the crude product by chromatography (silica gel, 1 to 2% methanol in methylene chloride) followed by pumping in vacuo afforded the titled intermediate as a viscous oil. $^1$H-NMR (400 MHz, $CDCl_3$) δ 7.39 (d, J=9.0 Hz, 2H), 7.24 (d, J=2.1 Hz, 1H), 7.13 (d-d, J=8.3 Hz, J=2.1 Hz, 1H), 6.85 (d, J=8.7, 2H), 6.84 (d, J=8.3 Hz, 1H), 4.81 (p, J=2.0 Hz, 1H), 4.09 (t, J=4.4 Hz, 2H), 4.00 (s, 4H), 3.97 (t, J=4.4 Hz, 2H), 3.84 (s, 3H), 2.3 to 1.5 (m, 21H with $H_2O$).

32c) 4-(3-cyclopentyloxy-4-methoxyphenyl)-4-(2-[4-(2-hydroxyethan-1-oxy)phenyl]ethynyl)cyclohexan-1-one A solution of 4-(3-cyclopentyloxy-4-methoxyphenyl)-4-(2-[4-(2-hydroxyethan-1-oxy)phenyl]ethynyl)-1,1-(ethylenedioxy)cyclohexane (0.090 g, 0.18 mmol) in tetrahydrofuran (8 mL) was treated with 3N hydrochloric acid (0.9 mL) as in Example 12. Purification by chromatography (silica gel, 40 to 50% ethyl acetate in hexanes) followed by drying in vacuo at 60° C. afforded the tided compound as a glass. Anal. ($C_{28}H_{32}O_5 \cdot 1/4\ H_2O$) calcd: C 74.23, H 7.23, found: C 74.31, H 7.24. $^1$H-NMR (400 MHz, $CDCl_3$) δ 7.41 (d, J=8.9 Hz, 2H), 7.23 (d, J=2.3 Hz, 1H), 7.13 (d-d, J=8.5 Hz, J=2.3 Hz, 1H), 6.89 (d, J=8.7, 2H), 6.86 (d, J=8.3 Hz, 1H), 4.80 (p, 1H), 4.11 (t, J=4.5 Hz, 2H), 3.98 (t, J=4.4 Hz, 2H), 3.85 (s, 3H), 3.04 (d-t, J=14.1 Hz, J=6.1 Hz, 2H), 2.47 (d,br, J=13.0, 2H), 2.4 to 1.5 (m, 19H with $H_2O$).

EXAMPLE 33

Preparation of 4-(4-carbomethoxyphenylethynyl)-4-(3-cyclopentyloxy-4-methoxyphenyl)cyclohexan-1-one 33a) 4-(4-carbomethoxyphenylethynyl)-4-(3-cyclopentyloxy-4-methoxyphenyl)-1,1-(ethylenedioxy) cyclohexane A stirred mixture of 4-(4-cyclopentyloxy-4-methoxyphenyl)-1,1-(ethylenedioxy)-4-ethynylcyclohexane (0.200 g, 0.56 mmol) and methyl 4-iodobenzoate (0.147 g, 0.56 mmol) in triethylamine (2.5 mL, dry) was treated with a mixture of tetrakis(triphenylphosphine)palladium (0.032 g, 0.028 mmol), cuprous iodide (0.0064 g, 0.034 mmol), and triphenylphosphine (crystal) by the procedure of Example 1d. The reaction mixture was extracted and chromatographed as described in Example 1d and stripped in vacui to afford a light yellow oil (0.25 g, 91%). $^1$H-NMR (400 MHz, $CDCl_3$) δ 7.98 (d, 9.4 Hz, 2H), 7.50 (d, J=9.4 Hz, 2H), 7.20 (d, J=1.9 Hz, 1H), 7.12 (d-d, J=1.9 Hz, J=8.6 Hz, 1H), 6.84 (d, J=8.6, 1H), 4.80 (p, J=3.8 Hz, 1H), 4.00 (s, br, 4H), 3.92 (s, 3H), 3.85 (s, 3H), 2.3 to 1.5 (m, 17H with $H_2O$).

33b) 4-(4-carbomethoxyphenylethynyl)-4-(3-cyclopentyloxy-4-methoxyphenyl)cyclohexane A stirred solution of 4-(4-carbomethoxyphenylethynyl)-4-(3-cyclopentyloxy-4-methoxyphenyl)-1,1-(ethylenedioxycyclohexane (0.150 g, 0.12 mmol) in tetrahydrofuran (7 mL) was treated with 3N hydrochloric acid (0.70 mL) as described in Example 14 above. The crude product was purified by chromatography (silica, 20% ethyl acetate/hexanes) and the solvent removed in vacuo to afford the titled compound as a resin (0.063 g, 46%). Anal. ($C_{28}H_{30}O_5 \cdot 1/10\ H_2O$) calcd: C 75.01, H 6.79, found: C 74.97, H 6.87. $^1$H-NMR (400 MHz, $CDCl_3$) δ 8.01 (d, J=8.5 Hz, 2H), 7.53 (d, J=8.5 Hz, 2H), 7.20 (d, J=2.4 Hz, 1H), 7.11 (d-d, J=8.5 Hz, J=2.4 Hz, 1H), 6.87 (d, J=8.5, 1H), 4.80 (p, 1H), 3.93 (s, 3H), 3.86 (s, 3H), 3.04 (d-t, J=6.2 Hz, J=14.4, 2H), 2.50 (d,br, J=14.9, 2H), 2.42–2.32 (m, 2H), 2.26 (d-t, J=2.8 Hz, J=14.4 Hz, 2H), 2.00–1.5 (m, 11H with $H_2O$).

EXAMPLE 34

Preparation of 4-(4-carboxyphenylethynyl)-4-(3-cyclopentyloxy-4-methoxyphenyl)cyclohexan-1-one A stirred solution of 4-(4-carbomethoxyphenylethynyl)-4-(3-cyclopentyloxy-4-methoxyphenyl)cyclohexane (0.146 g, 0.326 mmol) in dry methanol (5 mL) was treated with 10% aqueous sodium hydroxide solution (0.46 mL, 1.15 mmol) under an argon atmosphere as described in Example 13. The crude acid was purified by chromatography (silica, ethyl acetate/methylene chloride/formic acid; 10:90:1), the product fractions washed with water three times, was stripped in vacuo, was crystalized with ether and was dried in vacuo to afford the titled compound as a white solid (0.077 g, 55%), mp 170°–171° C. Anal. ($C_{27}H_{28}O_5$) calcd: C 74.98, H 6.53 found: C 74.78, H 6.54.

EXAMPLE 35

Preparation of 4-(3-cyclopentyloxy-4-methoxyphenyl)4-(2-[4-(1-piperidinocarbonylmethoxy)phenyl]ethynyl)cyclohexan-1-one 35a) 4-iodophenoxyacetic acid methyl ester A stirred mixture of 4-iodophenol (0.50 g, 2.27 mmol), methyl 2-bromoacetate (0.382 g, 2.50 mmol), and powdered potassium carbonate (0.314 g, 2.27 mmol) in dry acetone under argon was sealed and heated at 70° C. for 4 hr. The cooled mixture was filtered, and the filtrate was evaporated in vacuo. The residue was purified by chromatography (silica, 40 to 50% methylene chloride in cyclohexane) and the solvent was removed in vacuo to afford the titled intermediate as a white solid (0.41 g, 62%), mp 69°–70° C.

35b) 4-(3-cyclopentyloxy-4-methoxyphenyl)-1,1-(ethylenedioxy)-4-(2-[4-(1-piperidinocarbonylmethoxy)phenyl]ethynyl)cyclohexane A stirred mixture of 4-(3-cyclopentyloxy-4-methoxyphenyl)-1,1-(ethylenedioxy)-4-ethynylcyclohexane (0.150 g, 0.42 mmol) and 4-iodophenoxyacetic acid methyl ester (0.123 g, 0.42 mmol) in dry piperidine (2 mL) was treated at 80° C. for 1.5 hr by the procedure of Example 11 with a mixture of tetrakis(triphenylphosphine)palladium (0.027 g, 0.023 mmol), cuprous iodide (0.0048 g, 0.025 mmol), and triphenylphosphine (crystal). The crude product was chromatographed (silica 50 to 75% ethyl acetate in petroleum ether) and was stripped in vacuo to afford the titled intermediate as a viscous yellow oil (0.232 g, 96%). $^1$H-NMR (400 MHz, CDCl$_3$) δ 7.38 (d, J=8.7 Hz, 2H), 7.24 (d, J=2.3 Hz, 1H), 7.13 (d-d, J=8.4 Hz, J=2.3 Hz, 1H), 6.89 (d, J=8.9 Hz, 1H), 6.84 (d, J=8.4, 1H),4.81 (p, 1H), 4.69 (s, 2H), 4.00 (s, 4H), 3.84 (s, 3H), 3.56 (t, J=5.5 Hz, 2H), 3.49 (t, J=5.5 Hz, 2H), 2.3 to 1.5 (m, 32H with $H_2O$).

35c) 4-(3-cyclopentyloxy-4-methoxyphenyl)-4-(2-[4-(1-piperidinocarbonylmethoxy)phenyl]ethynyl)cyclohexan-1-one A stirred solution of 4-(3-cyclopentyloxy-4-methoxyphenyl)-1,1-(ethylenedioxy)-4-(2-[4-(1-piperidinocarbonylmethoxy)phenyl]ethynyl)cyclohexane (0.232 g, 0.40 mmol) in tetrahydrofuran (9 mL) was treated with 3N hydrochloric acid (0.90 mL) as described in Example 12 above. The crude product was purified by chromatography (silica, 50% ethyl acetate/hexanes) and the solvent removed in vacuo to afford the titled compound as a resin (0.127 g, 59%). Anal. ($C_{28}H_{30}O_5$.1/10 $H_2O$) calcd: C 75.01, H 6.79, found: C 74.97, H 6.87. $^1$H-NMR (400 MHz, CDCl$_3$) δ 7.41 (d, J=9.1 Hz, 2H), 7.22 (d, J=2.3 Hz, 1H), 7.11 (d-d, J=8.4 Hz, J=2.3 Hz, 1H), 6.92 (d, J=8.6, 1H), 6.86 (d, J=8.5, 1H),4.80 (p, 1H), 4.70 (s, 2H), 4.00 (s, 4H), 3.85 (s, 3H), 3.56 (t, J=5.5 Hz, 2H), 3.48 (t, J=5.5 Hz, 2H), 3.03 (d-t, J=6.1 Hz, J=14.3, 2H), 2.47 (d,br, J=14.9, 2H), 2.4–2.2 (m, 4H), 2.0 to 1.5 (m, 25H with $H_2O$).

EXAMPLE 36

Preparation of 4-(2-[4-carboxymethyloxyphenyl]ethynyl)-4-(3-cyclopenyloxy-4-methoxyphenyl)cyclohexan-1-one 19a) 4-(2-[4-Carbomethoxymethyloxyphenyl]ethynyl)-4-(3-cyclopentyloxy-4-methoxyphenyl)-1,1-(ethylenedioxy)cyclohexane A stirred mixture of 4-(3-cyclopentyloxy-4-methoxyphenyl)-1,1-(ethylenedioxy)-4-ethynylcyclohexane (0.075 g, 0.21 mmol) and 4-iodophenoxyacetic acid methyl ester (0.060 g, 0.21 mmol, prepared as described in Example 35a) in dry triethylamine (2 mL) was treated at 80° C. for 1.5 hr by the procedure of Example 11 with a mixture of tetrakis(triphenylphosphine)palladium (0.018 g, 0.016 mmol), cuprous iodide (0.004 g, 0.021 mmol), and triphenylphosphine (crystal). The crude product was chromatographed (silica 40 to 50% ethyl acetate in hexanes) and stripped in vacuo to afford the tided intermediate as a dark red oil (0.080 g, 73%). $^1$H-NMR (400 MHz, CDCl$_3$) δ 7.98 (d, 9.4 Hz, 2H), 7.50 (d, J=9.4 Hz, 2H), 7.20 (d, J=1.9 Hz, 1H), 7.12 (d-d, J=1.9 Hz, J=8.6 Hz, 1H), 6.84 (d, J=8.6 Hz, 1H), 4.80 (p, J=3.8 Hz, 1H), 4.00 (s, br, 4H), 3.92 (s, 3H), 3.85 (s, 3H), 2.3 to 1.5 (m, 17H with $H_2O$).

36b) 4-(2-[4-carboxymethyloxyphenyl]ethynyl)-4-(3-cyclopentyloxy-4-methoxyphenyl)dyclohexan-1-one A stirred solution of 4-(2-[4-carbomethoxymethyloxyphenyl]ethynyl)-4-(3-cyclopentyloxy-4-methoxyphenyl)-1,1-(ethylenedioxy)cyclohexane (0.232 g, 0.40 mmol) in tetrahydrofuran (9 mL) was treated with 3N hydrochloric acid (0.90 mL) as described in Example 12 above. The crude product was purified by chromatography (silica, 50% ethyl acetate/hexanes) and the solvent removed in vacuo to afford the tided compound as a resin (0.127 g, 59%). Anal. ($C_{28}H_{30}O_5$.1/10 $H_2O$) calcd: C 75.01, H 6.79, found: C 74.97, H 6.87. $^1$H-NMR (400 MHz, CDCl$_3$) δ 8.01 (d, J=8.5 Hz, 2H), 7.53 (d, J=8.5 Hz, 2H), 7.20 (d, J=2.4 Hz, 1H), 7.11 (d-d, J=8.5 Hz, J=2.4 Hz, 1H), 6.87 (d, J=8.5, 1H), 4.80 (p, 1H), 3.93 (s, 3H), 3.86 (s, 3H), 3.04 (d-t, J=6.2 Hz, J=14.4, 2H), 2.50 (d,br, J=14.9, 2H), 2.42–2.32 (m, 2H), 2.26 (d-t, J=2.8 Hz, J=14.4 Hz, 2H), 2.00–1.5 (m, 11H with $H_2O$).

EXAMPLE 37

Preparation of 4-(2-[4-carbomethoxymethyloxyphenyl]ethynyl)-4-(3-cyclopentyloxy-4-methoxyphenyl)cyclohexan-1-one A stirred mixture of 4-(3-cyclopentyloxy-4-methoxyphenyl)-4-ethynylcyclohexan-1-one (0.075 g, 0.24 mmol) and 4-iodophenoxyacetic acid methyl ester (0.070 g, 0.24 mmol, prepared as described in Example 35a) in dry triethylamine (1.2 mL) was treated at 75° C. for 1 hr with a mixture of tetrakis(triphenylphosphine)-palladium (0.012 g, 0.010 mmol), cuprous iodide (0.0024 g, 0.013 mmol), and triphenylphosphine (a small crystal) under argon. The reaction mixture was concentrated in vacuo and the residue treated with cold dilute hydrochloric acid, was extracted twice with ethyl acetate and the organic phase was washed with water, brine and was dried over anhydrous sodium sulfate. The crude product was chromatographed (silica, 25 to 30% ethyl acetate in hexanes) and was stripped in vacuo to afford the titled intermediate as an amber resin (0.097 g, 85%). Anal. ($C_{29}H_{32}O_6$) calcd: C 73.09, H 6.77, found: C 72.91, H 6.78. $^1$H-NMR (400 MHz, $CDCl_3$) δ 7.41 (d, J=8.9 Hz, 2H), 7.21 (d, J=2.2 Hz, 1H), 7.11 (d-d, J=1.9 Hz, J=8.4 Hz, 1H), 6.87 (d, J=8.9, 2H), 6.85 (d, J=8.4, 1H), 4.80 (p, J=4.4 Hz, 1H), 4.65 (s, 2H), 3.84 (s, 3H), 3.81 (s, 3H), 3.02 (d-t, J=6.2 Hz, J=14.2, 2H), 2.46 (d,br, J=14.8, 2H), 2.4–1.5 (m, 16H with $H_2O$).

EXAMPLE 38

Preparation of 4-(2-carbomethoxyphenylethynyl)-4-(3-cyclopenyloxy-4-methoxyphenyl)cyclohexan-1-one A mixture of 4-(4-cyclopentyloxy-4-methoxyphenyl)-4-ethynylcyclohexan-1-one (0.150 g, 0.48 mmol) and methyl 2-iodobenzoate (0.126 g, 0.48 mmol) in triethylamine (2.4 mL, dry) was treated with a mixture of tetrakis(triphenylphosphine)palladium(0) (0.024 g, 0.021 mmol), cuprous iodide (0.0048 g, 0.026 mmol), and triphenylphosphine (crystal) under an argon atmosphere and stirred at 80° C. for 7 h. The reaction mixture was concentrated in vacuo, and the residue treated as described in example 20, chromatographed twice (silica, 20% ethyl acetate in hexanes; and 2% ethyl acetate in methylene chloride) crystallized from ether:hexanes and dried at 60° C. in vacuo to afford a white powder (0.051 g, 24%), mp 88.5°–90° C. Anal. ($C_{28}H_{30}O_5$) calcd: C 75.31, H 6.77, found: C 75.11, H 6.78.

EXAMPLE 39

Preparation of 4-(3-cyclopentyloxy-4-methoxyphenyl)-4-(2-[3,5-dicarbomethoxyphenyl]ethynyl)cyclohexan-1-one A mixture of 4-(4-cyclopentyloxy-4-methoxyphenyl)-4-ethynylcyclohexan-1-one (0.075 g, 0.24 mmol) and dimethyl 5-iodoisophthalate (Trans World Chemicals, 0.107 g, 0.33 mmol) in triethylamine (1.9 mL, dry) was treated with a mixture of tetrakis(triphenylphosphine)palladium (0.012 g, 0.010 mmol), cuprous iodide (0.0025 g, 0.013 mmol), and triphenylphosphine (a small crystal) under an argon atmosphere and was stirred at 80° C. for 1 h. The reaction mixture was concentrated in vacuo, and the residue was chromatographed (silica, 1 to 2% ethyl acetate in methyiene chloride) and was dried at 50° C. in vacuo to afford a tan powder (0.100 g, 83%), mp 133.5°–135° C. Anal. ($C_{30}H_{33}O_7$) calcd: C 71.41, H 6.39, found: C 71.19, H 6.41.

EXAMPLE 40

Preparation of 4-(2-[4-chlorophenyl]ethynyl)-4-(3-cyclopentyloxy-4-methoxyphenyl)cyclohexan-1-one A mixture of 4-(4-yclopentyloxy-4-methoxyphenyl)-4-ethynylcyclohexan-1-one (0.075 g, 0.24 mmol) and 4-chloro-1-iodobenzene (0.057 g, 0.24 mmol) in triethylamine (1.7 mL, dry) was treated with a mixture of tetrakis(triphenylphosphine)palladium (0.012 g, 0.010 mmol), cuprous iodide (0.0025 g, 0.013 mmol), and triphenylphosphine (a small crystal) under an argon atmosphere and was stirred at 80° C. for 2 h. The reaction mixture was concentrated in vacuo, and the residue treated with dilute hydrochloric acid, was extracted three times with ethyl acetate and the organic phase was dried over sodium sulfate and was concentrated in vacuo. The residue was chromatographed (silica, 0.05 to 1% ethyl acetate in methylene chloride/ hexanes 3:1) and the tided compound was dried at 25° C. in vacuo to afford a white powder (0.051 g, 50%), mp 104°–105° C. Anal. ($C_{26}H_{27}ClO_3$) calcd: C 73.83, H 6.43, found: C 73.69, H 6.41.

EXAMPLE 41

Preparation of 4-(3-cyclopentyloxy-4-methoxyphenyl)-4-(2-[3-(5-methyl-[1,2,4]oxadiazol-3-yl)phenyl]ethynyl)cyclohexan-1-one 41a) 3-(3-iodophenyl)-5-methyl-[1,2,4]oxadiazole 3-(3-Iodophenyl)-5-methyl-[1,2,4]oxadiazole was prepared by standard chemistry well known to those versed in the art and is a white solid, mp 90°–91.5° C. 41b) 4-(3-cyclopentyloxy-4-methoxyphenyl)-4-(2-[3-(5-methyl-[1,2,4]oxadiazol-3-yl)phenyl]ethynyl)cyclohexan-1-one A stirred mixture of 4-(3-cyclopentyloxy-4-methoxyphenyl)-4-ethynylcyclohexan-1-one (0.200 g, 0.64 mmol) and 3-(3-iodophenyl)-5-methyl-[1,2,4]oxadiazole (0.201 g, 0.70 mmol) in dry triethylamine (4.6 mL) was treated with a mixture of tetrakis(triphenylphosphine) palladium (0.032 g, 0.028 mmol), cuprous iodide (0.0067 g, 0.035 mmol), and triphenylphosphine (a small crystal) at 75° C. for 1 h 20 min under argon. The reaction mixture was concentrated in vacuo and the residue was treated with cold dilute hydrochloric acid, was extracted twice with methylene chloride and the organic phase was washed with water, brine and was dried over anhydrous sodium sulfate. The crude product was chromatographed (silica, 3 to 6% ethyl acetate in methylene chloride/hexanes 4:1) and the pure fractions were combined, concentrated in vacuo , was crystallized from ethyl ether and was dried at 60° C. in vacuo to afford the titled compound as a white solid (0.235 g, 78%), mp 122.5°–123.5° C. Anal. ($C_{29}H_{30}N_2O_4$) calcd: C 74.02, H 6.43, N 5.95, found: C 73.94, H 6.37, N 5.96.

EXAMPLE 42

Preparation of 4-(3-cyclopentyloxy-4-methoxyphenyl)-4-(2-[3-(3-methyl-[1,2,4]oxadiazole-5-yl)phenyl]ethynyl)cyclohexan-1-one 42a) 5-(3-iodophenyl)-3-methyl-[1,2,4]oxadiazole 5-(3-Iodophenyl)-3-methyl-[1,2,4]oxadiazole was prepared by standard chemistry well known to those versed in the art and was a white solid, mp 102°–103° C.
42b) 4-(3-cyclopentyloxy-4-methoxyphenyl)-4-(2-[3-(3-methyl-[1,2,4]oxadiazole-5-yl)phenyl]ethynyl)cyclohexan-1-one A stirred mixture of 4-(3-cyclopentyloxy-4-methoxyphenyl)-4-ethynylcyclohexan-1-one (0.200 g, 0.64 mmol) and 5-(3-iodophenyl)-3-methyl-[1,2,4]oxadiazole (0.201 g, 0.70 mmol) in dry triethylamine (4.6 mL) was treated under argon with a mixture of tetrakis (triphenylphosphine)palladium (0.032 g, 0.028 mmol), cuprous iodide (0.0067 g, 0.035 mmol), and triphenylphosphine (a small crystal) at 70° C. for 1 h and at 25° C. for 15 h. The reaction mixture was concentrated in vacuo and a solution of the residue was dissolved in methylene chloride, was treated with cold dilute hydrochloric acid and was dried over anhydrous sodium sulfate. The crude product was chromatographed (silica, 5 to 10% ethyl acetate in methylene chloride/hexanes 1:1) and the pure fractions were combined, concentrated in vacuo, crystallized from ethyl ether and dried at 60° C. in vacuo to afford the titled compound as an off-white powder (0.235 g, 78%), mp 88°–91° C. Anal. ($C_{29}H_{30}N_2O_4$) calcd: C 74.02, H 6.43, N 5.95, found: C 73.77, H 6.53, N 5.78.

EXAMPLE 43

Preparation of 4-(2-[3-cyanophenyl]ethynyl)-4-(3-cyclopentyloxy-4-methoxyphenyl)cyclohexan-1-one A mixture of 4-(4-cyclopentyloxy-4-methoxyphenyl)-4-ethynylcyclohexan-1-one (0.100 g, 0.32 mmol) and 3-iodobenzonitrile (0.088 g, 0.38 mmol) in triethylamine (2.5 mL, dry) was treated with a mixture of tetrakis (triphenylphosphine)palladium (0.016 g, 0.013 mmol), cuprous iodide (0.0033 g, 0.017 mmol), and triphenylphosphine (a small crystal) under an argon atmosphere and was stirred at 75° C. for 1 h 15 min, followed by ambient temperature for 15 h. The reaction mixture was concentrated in vacuo, and a solution of the residue was dissolved in methylene chloride, was washed with dilute hydrochloric acid, water, brine and was dried over sodium sulfate. The crude product was chromatographed (silica, 3% ethyl acetate in methylene chloride/hexanes 4:1) and the titled compound was dried at 60° C. in vacuo to afford a white solid (0.075 g, 47%), mp 123.5°–125.5° C. Anal. ($C_{27}H_{27}NO_3$) calcd: C 78.42, H 6.58, N 3.39, found: C 78.13, H 6.67, N 3.40.

EXAMPLE 44

Preparation of 4-(3-cyclopentyloxy-4-methoxyphenyl)-4-(2-[3,5-dicyanophenyl]ethynyl) cyclohexan-1-one 44a) 3,5-dicyanophenyl iodide 3,5-Dicyanophenyl iodide was prepared by standard chemistry well known to those versed in the art and was a white solid, mp 145.5°–146.5° C.

44-b) 4-(3-cyclopentyloxy-4-methoxyphenyl)-4-(2-[3,5dicyanphenyl]ethynyl)cyclohexan-1-one A mixture of 4-(4-cyclopentyloxy-4-methoxyphenyl)-4-ethynylcyclohexan-1-one (0.150 g, 0.48 mmol) and 3,5-dicyanophenyl iodide (0.171 g, 0.67 mmol) in triethylamine (7.5 mL, dry) was treated with a mixture of tetrakis (triphenylphosphine)palladium (0.024 g, 0.021 mmol), cuprous iodide (0.005 g, 0.026 mmol), and triphenylphosphine (a small crystal) under an argon atmosphere and was stirred at 80° C. for 0.5 h and at 25° C. for 15 h. The reaction mixture was concentrated in vacuo, and a solution of the residue dissolved in methylene chloride was washed with dilute hydrochloric acid, water, brine and was dried over sodium sulfate. The residue was chromatographed (silica, 2 to 3% ethyl acetate in methylene chloride/hexanes 9:1) and was dried in vacuo to afford a white powder (0.177 g, 84%), mp 147.5°–148.5° C. Anal. ($C_{28}H_{26}N_2O_3$) calcd: C 76.69, H 5.98, N 6.39, found: C 76.41, H 5.92, N 6.39.

EXAMPLE 45

Preparation of 4-(3-cyclopentyloxy-4-methoxyphenyl)-4-(2-[4-hydroxyphenyl]ethynyl) cyclohexan-1-one A mixture of 4-(4-cyclopentyloxy-4-methoxyphenyl)-4-ethynylcyclohexan-1-one (0.090 g, 0.29 mmol) and 4-iodophenol (0.076 g, 0.35 mmol) in triethylamine (3 mL, dry) was treated with a mixture of tetrakis (triphenylphosphine)palladium (0.013 g, 0.012 mmol), cuprous iodide (0.003 g, 0.016 mmol), and triphenylphosphine (a small crystal) under an argon atmosphere and stirred at 75° C. for 40 min. The reaction mixture was concentrated in vacuo, and a solution of the residue dissolved in methylene chloride was washed with dilute hydrochloric acid, water, brine, was dried over sodium sulfate and was concentrated in vacuo. The residue was chromatographed (silica, 4 to 7% ethyl acetate in methylene chloride/ hexanes 4:1) and the tided compound was recrystallized from methanol to afford a white powder (0.035 g, 30%), mp 144°–146° C. Anal. ($C_{26}H_{28}O_4 \cdot 1/5\ H_2O$) calcd: C 76.52, H 7.01, found: C 76.57, H 6.97. $^1$H-NMR (400 MHz, CDCl$_3$) δ 7.36 (d, 8.5 Hz, 2H), 7.23 (d, J=2.2 Hz, 1H), 7.12 (d-d, J=2.2 Hz, J=8.5 Hz, 1H), 6.86 (d, J=8.5, 1H), 6.80 (d, J=8.5, 2H), 5.22 (s, 1H), 4.80 (p, J=3.8 Hz, 1H), 3.85 (s, 3H), 3.04 (d-t, J=6.0 Hz, J=14.2, 2H), 2.47 (d,br, J=14.8, 2H), 2.4–2.1 (m, 4H), 2.0 to 1.5 (m, 12H with $H_2O$).

EXAMPLE 46

Preparation of 4-(3-cyclopentyloxy-4-methoxyphenyl)-4-(2-[3-(5-methyl-[1,3,4]thiadiazol-2-yl)phenyl]ethynyl)cyclohexan-1-one 46a) 2-(3-iodophenyl)-5-methyl-[1,3,4]thiadiazole 2-(3-Iodophenyl)-5-methyl-[1,3,4]thiadiazole was prepared by standard chemistry well known to those versed in the art.

46b) 4-(3-cyclopentyloxy-4-methoxyphenyl)-4-(2-[3-(5-methyl-[1,3,4]thiadiazol-2-yl)phenyl]ethynyl)cyclohexan-1-one A stirred mixture of 4-(3-cyclopentyloxy-4-methoxyphenyl)-4-ethynylcyclohexan-1-one (0.100 g, 0.32 mmol) and 2-(3-iodophenyl)-5-methyl-[1,3,4]thiadiazole (0.097 g, 0.32 mmol) in dry triethylamine (2.5 mL) was treated under argon with a mixture of tetrakis (triphenylphosphine)palladium (0.016 g, 0.013 mmol), cuprous iodide (0.0033 g, 0.017 mmol), and triphenylphosphine (a small crystal) at 70° C. for 1 h and at 25° C. for 15 h. The reaction mixture was concentrated in vacuo and the residue was partitioned between methylene chloride and cold dilute hydrochloric acid. The organic phase was chromatographed (silica, 10 to 20% ethyl acetate in methylene chloride) and the pure fractions were combined, concentrated in vacuo and dried at 50° C. in vacuo and the brittle resin ground to afford the titled compound as a yellow powder (0.128 g, 79%). Anal. ($C_{29}H_3ON_2)_3S \cdot H_2O$) calcd: C 69.02, H 6.39, N 5.55, found: C 68.91, H 6.21, N 5.35. $^1$H-NMR (400 MHz, CDCl$_3$) δ 8.06 (t, J=1.6 Hz, 1H), 7.88 (d-t, J=1.4 Hz, J=8.1 Hz, 1H), 7.58 (d-d, J=1.2 Hz, J=9.0 Hz, 1H), 7.45 (t, J=7.8 Hz), 7.21 (d, J=2.2, 1H), 7.14 (dd, J=8.4 Hz, J=2.1 Hz, 1H), 6.88 (d, J=8.5, 1H), 4.82 (p, J=4.1 Hz, 1H), 3.86 (s, 3H), 3.04 (d-t, J=6.1 Hz, J=14.2, 2H), 2.84 (s, 3H), 2.50 (d,br, J=14.9, 2H), 2.42–2.32 (m, 2H), 2.27 (d-t, J=2.8 Hz, J=14.2 Hz, 2H), 2.00–1.5 (m, 12H with $H_2O$).

EXAMPLE 47

Preparation of 4-(3-cyclopentyloxy-4-methoxyphenyl)-4-(2-[3-(5-methyl-[1,3,4]oxadiazol-2-yl)phenyl]ethynyl)cyclohexan-1-one 47a) 2-(3-iodophenyl)-5-methyl-[1,3,4]oxadiazole 2-(3-Iodophenyl)-5-methyl-[1,3,4]oxadiazole was prepared by standard chemistry well known to those versed in the art and was a white solid, mp 112.5°–113.5° C.

47b) 4-(3-cyclopentyloxy-4-methoxyphenyl)-4-(2-[3-(5-methyl-[1,3,4]oxadiazol-2-yl)phenyl]ethynyl)cyclohexan-1-one A stirred mixture of 4-(3-cyclopentyloxy-4-methoxyphenyl)-4-ethynylcyclohexan-1-one (0.100 g, 0.32 mmol) and 5-(3-iodophenyl)-2-methyl-[1,3,4]oxadiazole (0.0915 g, 0.32 mmol) in dry triethylamine (3.5 mL) was treated under argon with a mixture of tetrakis(triphenylphosphine)palladium (0.016 g, 0.013 mmol), cuprous iodide (0.0033 g, 0.017 mmol), and triphenylphosphine (a small crystal) at 75° C. for 1 h. The reaction mixture was concentrated in vacuo, the residue was extracted into methylene chloride and the organic phase was washed with cold dilute hydrochloric acid, water, brine and was dried (sodium sulfate). Purification by chromatography (silica, 10 to 20% ethyl acetate in methylene chloride) followed by drying at 50° C. in vacuo afforded the titled compound as a white powder (0.068 g, 45%), mp 139°–141° C. Anal. ($C_{29}H_{30}N_2O_4$.1/3$H_2O$) calcd: C 73.09, H 6.49, N 5.88, found: C 73.07, H 6.35, N 5.79. $^1$H-NMR (400 MHz, $CDCl_3$) δ 8.15 (t, J=1.6 Hz, 1H), 8.01 (d-t, J=1.4 Hz, J=7.9 Hz, 1H), 7.62 (d-d, J=1.5 Hz, J=7.8 Hz, 1H), 7.49 (t, J=7.9 Hz), 7.21 (d, J=2.3, 1H), 7.14 (d-d, J=8.5 Hz, J=2.4 Hz, 1H), 6.88 (d, J=8.5, 1H), 4.82 (p, J=4.2 Hz, 1H), 3.86 (s, 3H), 3.04 (d-t, J=6.1 Hz, J=14.2, 2H), 2.64 (s, 3H), 2.51 (d,br, J=15.0, 2H), 2.42–2.32 (m, 2H), 2.27 (d-t, J=2.8 Hz, J=14.2 Hz, 2H), 2.00–1.5 (m, 9H with $H_2O$).

EXAMPLE 48

Preparation of 4-(3-cyclopentyloxy-4-methoxyphenyl)-4-(2[E]-(3-cyanophenyl)ethenyl)cyclohexan-1-one 48a) 3-cyanobenzylphosphonic acid diethyl ester A stirrd mixture of triethyl phosphite (0.500 g, 2.95 mmol) and 3-cyanobenzyl bromide (0.609 g, 2.95 mmol) was refluxed at 140° C. under argon for 2 h and the resulting volatiles were removed at room temperature in vacuo to afford the tided intermediate as a colorless oil (0.62 g, 84%). $^1$H-NMR (400 MHz, $CDCl_3$) δ 7.7–7.5 (m, 3H), 7.44 (t, J=7.8 Hz, 1H), 4.06 (p, J=7.6 Hz, 4H), 3.17 (d J=21.8 Hz, 2H), 1.27 (t, J=7.1 Hz, 6H).

48b) 4-(3-cyclopentyloxy-4-methoxyphenyl)-4-(2[E]-(3-cyanophenyl)ethenyl)-1,1-(ethylenedioxy)cyclohexane A solution of 3-cyanobenzylphosphonic acid diethyl ester (0.54 g, 2.13 mmol) dissolved in dry tetrahydrofuran (7 mL) was added via cannulation to a solution of potassium t-butoxide (0.237 g, 2.11 mmol) dissolved in dry tetrahydrofuran (15 mL), both solutions under argon and was chilled to 0° C. After stirring for 45 min, a solution of 4-4-(3-cyclopentyloxy-4-methoxyphenyl)-1,1-(ethylenedioxy)-4-formylcyclohexane (0.38 g, 1.06 mmol) in dry tetrahydrofuran (5 mL) was added dropwise. The reaction mixture was allowed to warm to room temperature. After 15 h, the mixture was quenched with aqueous ammonium chloride solution, was concentrated in vacuo, was partitioned between methylene chloride/aqueous ammonium chloride solution, and the organic extract was washed with water, brine, was dried (sodium sulfate), and was concentrated in vacuo to afford a mixture containing the desired titled product and the excess phosphonate ester as a crude resin. $^1$H-NMR (400 MHz, $CDCl_3$) δ 7.62–7.4 (m, 4H), 7.36 (t, J=7.8 Hz, 1H), 6.90 (s and d, 2H), 6.83 (d, J=8.7 Hz, 1H), 6.30 (d, J=16.4 Hz, 1H), 6.16 (d, J=16.3 Hz, 1H), 4.75 (p, J=4.4 Hz, 1H), 4.06 (p, J=7.6 Hz, 1H), 3.96 (q, J=3.3 Hz, 4H), 3.84 (s, 3H), 3.17 (d J=21.8 Hz, 0.3H), 2.35–1.5 (m, 20H with $H_2O$), 1.27 (t, J=7.1 Hz, 1.3H 48c) 4-(3-cyclopentyloxy-4-methoxyphenyl)-4-(2[E]-(3-cyanophenyl)ethenyl)cyclohexan-1-one A solution of crude 4-(3-cyclopentyloxy-4-methoxyphenyl)-4-(2[E]-(3-cyanophenyl)ethenyl)-1,1-(ethylenedioxy)cyclohexane (0.58 g, 1.06 mmol) in tetrahydrofuran (20 mL) was treated with 3N aqueous hydrochloric acid (2.3 mL) under argon and heated at 75°–80° C. for 1 h. Additional hydrochloric acid (13 mL) was then added and the mixture heated at 75° C. for another 15 min. The reaction mixture was concentrated in vacuo, was extracted into methylene chloride, and the organic extract was washed with water, dilute sodium bicarbonate solution, brine, and was dried (sodium sulfate). Purification by chromatography (silica, 1 to 2% ethyl acetate in methylene chloride) and crystallization from ethyl ether gave the tided compound as a white solid (0.329 g, 74%). mp 116°–117° C. Anal. ($C_{27}H_{29}NO_3$.1/6$H_2O$) calcd: C 77.48, H 7.06, N 3.35, found: C 77.63, H 6.94, N 3.33. $^1$H-NMR (400 MHz, $CDCl_3$) δ 7.60 (s, 1H), 7.55–7.45 (m, 2H), 7.39 (t, J=7.7 Hz, 1H), 6.97 (dd, J=2.4 Hz, J=8.5 Hz, 1H), 6.89 (d, J=8.4 Hz, 1H), 6.37 (d, J=16.1 Hz, 1H), 6.22 (d, J=16.2 Hz, 1H), 4.77 (p, J=4.5 Hz, 1H), 3.86 (s, 3H), 2.6–1.5 (m, 18H with $H_2O$).

EXAMPLE 49

Preparation of 4-(2-acetamidopyrimidin-5-ylethynyl)-4-(3-cylopentyloxy-4-methoxyphenyl)cyclohexan-1-one, SB 240712

To a stirred suspension of pyridinium chlorochromate (0.288 g, 1.34 mmol) in dry methylene chloride (4 mL) under argon was added via cannula, a solution of cis-[4-(2-acetamidopyrimidin-5-ylethynyl)-4-(3-cyclopentyloxy-4-methoxyphenyl)cyclohexan-1-ol] (0.20 g, 0.445 mmol, prepared as described in a co-pending U.S. application identified as P50287 (filed on even day herewith) in methylene chloride (5 mL total). After 2 h at 25° C., ethyl acetate (ca. 10 mL) was added, the reaction filtered, and the precipitate washed with another 10 mL of ethyl acetate. The filtrate was concentrated and the residue purified by flash chromatography on silica gel with 1:9 ethyl acetate:dichloromethane, eluting the product with 20:80 to 30:70 ethyl acetate:dichloromethane to provide 4-(2-acetamidopyrimidin-5-yl-ethynyl)-4-(3-cyclopentyloxy-4-methoxyphenyl)cyclohexan-1-one as a white solid (0.033 g, 5.5%), mp 170°–171° C. $^1$H-NMR (400 MHz, $CDCl_3$) δ 8.65 (s, 2H), 8.47 (s, 1H), 7.14 (d, J=2.1 Hz, 1H), 7.09 (dd, J=8.4, 2.3 Hz, 1H), 6.87 (d, J=8.5 Hz, 1H), 4.80 (p, J=4.7, 1H), 3.86 (s, 3H), 2.94 (dt, J=23, 8.8 Hz, 2H), 2.50 (s superimposed upon 2.6–2.2 m, 9H), 2.0–1.5 (m, superimposed upon water) ppm.

EXAMPLE 50

Proceeding in a manner set forth in any one or more of the preceeding examples, the following compounds may be prepared:

4-(3-cyclopentyloxy-4-methoxyphenyl)-4-(2-[3-(5-trifluoromethyl[1,2,4]oxadiazol-3-yl)phenyl]ethynyl)cyclohexan-1-one, 4-(3-cyclopentyloxy-4-methoxyphenyl)-4-(2-[3-(3-trifluoromethyl[1,2,4]oxadiazol-5-yl)phenyl]ethynyl)cyclohexan-1-one, 4-(3-cyclopentyloxy-4-methoxyphenyl)-4-(2-[3-(5-trifluoromethyl[1,3,4]oxadiazol-2-yl)phenyl]ethynyl)cyclohexan-1-one, 4-(3-cyclopentyloxy-4-methoxyphenyl)-4-(2-[3-(5-trifluoromethyl[1,3,4]thiadiazol-2-yl)phenyl]ethynyl)cyclohexan-1-one, and 4-(3-cyclopentyloxy-4-methoxyphenyl)-4-(2-[2-acetamidopyrimidin-5-yl]ethynyl)cyclohexan-1-one.

UTILITY EXAMPLES

EXAMPLE A

Inhibitory effect of compounds of Formula (I) and (II) on in vitro TNF production by human monocytes The inhibitory effect of compounds of Formula (I) and (II) on in vitro TNF production by human monocytes may be determined by the protocol as described in Badger et al., EPO published Application 0 411 754 A2, Feb. 6, 1991, and in Hanna, WO 90/15534, Dec. 27, 1990.

EXAMPLE B

Two models of endotoxic shock have been utilized to determine in vivo TNF activity for the compounds of Formula (I) and (I). The protocol used in these models is described in Badger et al., EPO published Application 0 411 754 A2, Feb. 6, 1991, and in Hanna, WO 90/15534, Dec. 27, 1990.

The compound of Example 1 herein demonstrated a positive in vivo response in reducing serum levels of TNF induced by the injection of endotoxin.

EXAMPLE C

Isolation of PDE Isozymes

The phosphodiesterase inhibitory activity and selectivity of the compounds of Formula (I) and (II) can be determined using a battery of five distinct PDE isozymes. The tissues used as sources of the different isozymes are as follows: 1) PDE Ib, porcine aorta; 2) PDE Ic, guinea-pig heart; 3) PDE III, guinea-pig heart; 4) PDE IV, human monocyte; and 5) PDE V (also called "Ia"), canine trachealis. PDEs Ia, Ib, Ic and III are partially purified using standard chromatographic techniques [Torphy and Cieslinski, Mol. Pharmacol., 37:206–214, 1990]. PDE IV is purified to kinetic homogeneity by the sequential use of anion-exchange followed by heparin-Sepharose chromatography [Torphy et al., J. Biol. Chem., 267:1798–1804, 1992].

Phosphodiesterase activity is assayed as described in the protocol of Torphy and Cieslinski, Mol. Pharmacol., 37:206–214, 1990. Positive $IC_{50}$'s in the nanomolar to $\mu M$ range for compounds of the workings examples described herein for Formula (I) and (II) have been demonstrated.

What is claimed is:

1. A compound of Formula I

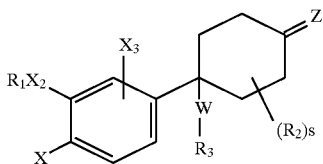

(I)

wherein:

$R_1$ is —$(CR_4R_5)_nC(O)O(CR_4R_5)_mR_6$, —$(CR_4R_5)_nC(O)NR_4(CR_4R_5)_mR_6$, —$(CR_4R_5)_nO(CR_4R_5)_mR_6$, or —$(CR_4R_5)_rR_6$ wherein the alkyl moieties may be unsubstituted or substituted with one or more fluorines;

m is 0 to 2;

n is 0 to 4;

r is 0 to 6;

$R_4$ and $R_5$ are independently hydrogen or $C_{1-2}$ alkyl;

$R_6$ is hydrogen, methyl, hydroxyl, aryl, halo substituted aryl, aryloxy$C_{1-3}$ alkyl, halo substituted aryloxy$C_{1-3}$ alkyl, indanyl, indenyl, $C_{7-11}$ polycycloalkyl, tetrahydrofuranyl, furanyl, tetrahydropyranyl, pyranyl, tetrahydrothienyl, thienyl, tetrahydrothiopyranyl, thiopyranyl, $C_{3-6}$ cycloalkyl, or a $C_{4-6}$ cycloalkyl containing one or two unsaturated bonds, wherein the cycloalkyl or heterocyclic moiety may be unsubstituted or substituted by 1 to 3 methyl groups, one ethyl group or an hydroxyl group;

provided that:

a) when $R_6$ is hydroxyl, then m is 2; or
b) when $R_6$ is hydroxyl, then r is 2 to 6; or
c) when $R_6$ is 2-tetrahydropyranyl, 2-tetrahydrothiopyranyl, 2-tetrahydrofuranyl, or 2-tetrahydrothienyl, then m is 1 or 2; or
d) when $R_6$ is 2-tetrahydropyranyl, 2-tetrahydrothiopyranyl, 2-tetrahydrofuranyl, or 2-tetrahydrothienyl, then r is 1 to 6;
e) when n is 1 and m is 0, then $R_6$ is other than H in —$(CR_4R_5)_nO(CR_4R_5)_mR_6$;

X is $YR_2$, fluorine, $NR_4R_5$, or formyl amine;

Y is O or $S(O)_{m'}$;

m' is 0, 1, or 2;

$X_2$ is O or $NR_8$;

$X_3$ is hydrogen or X;

$R_2$ is —$CH_3$ or —$CH_2CH_3$ unsubstituted or substituted by 1 or more fluorines;

s is 0 to 4;

$R_3$ is $COOR_{14}$, $C(O)NR_4R_{14}$ or $R_7$;

W is alkyl of 2 to 6 carbons, alkenyl of 2 to 6 carbon atoms or alkynyl of 2 to 6 carbon atoms;

Z is O, $NR_7$, $NCR_4R_5C_{2-6}$ alkenyl, $NOR_{14}$, $NOR_{15}$, $NOCR_4R_5C_{2-6}$ alkenyl, $NNR_4R_{14}$, $NNR_4R_{15}$, NCN, $NNR_8C(O)NR_8R_{14}$, $NNR_8C(S)NR_8R_{14}$, or =Z is 2-(1,3-dithiane), 2-(1,3dithiolane), dimethylthio ketal, diethylthio ketal, 2-(1,3-dioxolane), 2(1,3-dioxane), 2-(1,3-oxathiolane), dimethyl ketal or diethyl ketal;

$R_7$ is —$(CR_4R_5)_qR_{12}$ or $C_{1-6}$ alkyl wherein the $R_{12}$ or $C_{1-6}$ alkyl group is unsubstituted or substituted one or more times by methyl or ethyl unsubstituted or substituted by 1–3 fluorines, —F, —Br, —Cl, —$NO_2$, —$NR_{10}R_{11}$, —$C(O)R_8$, —$CO_2R_8$, —$O(CH_2)_{2-4}OR_8$, —$O(CH_2)_qR_8$, —CN, —$C(O)NR_{10}R_{11}$, —$O(CH_2)_qC(O)NR^{10}R_{11}$, —$O(CH_2)_qC(O)R_9$, —$NR_{10}C(O)NR_{10}R_{11}$, —$NR_{10}C(O)R_{11}$, —$NR_{10}C(O)OR_9$, —$NR_{10}C(O)R_{13}$, —$C(NR_{10})NR_{10}R_{11}$, —C(NCN)$NR_{10}R_{11}$, —C(NCN)$SR_9$, —$NR_{10}C(NCN)SR_9$, —$NR_{10}C(NCN)NR_{10}R_{11}$, —$NR_{10}S(O)_2R_9$, —$S(O)_{m'}R_9$, —$NR_{10}C(O)C(O)NR_{10}R_{11}$, —$NR_{10}C(O)C(O)R_{10}$, or $R_{13}$;

q is 0, 1, or 2;

$R_{12}$ is $R_{13}$, $(CH_2)_q$, $C_3-C_7$ cycloalkyl, (2-, 3- or 4-pyridyl), pyriridyl, pyrazolyl, (1- or 2-imidazolyl), pyrrolyl, piperazinyl, piperidinyl, morpholinyl, furanyl, (2- or 3-thienyl), quinolinyl, naphthyl, or phenyl;

$R_8$ is hydrogen or $R_9$;

$R_9$ is $C_{1-4}$ alkyl unsubstituted or substituted by one to three fluorines;

$R_{10}$ is $OR_8$ or $R_{11}$;

$R_{11}$ is hydrogen, or $C_{1-4}$ alkyl unsubstituted or substituted by one to three fluorines; or when $R_{10}$ and $R_{11}$ are as $NR_{10}R_{11}$ they may together with the nitrogen form a 5 to 7 membered ring comprised only of carbon atoms or carbon atoms and at least one heteroatom selected from O, N, or S;

$R_{13}$ is oxazolidinyl, oxazolyl, thiazolyl, pyrazolyl, triazolyl, tetrazolyl, imidazolyl, imidazolidinyl, thiazolidinyl, isoxazolyl, oxadiazolyl, or thiadiazolyl, and each of these heterocyclic rings is connected through a carbon atom and each may be unsubstituted or substituted by one or two C<sub>1-2</sub> alkyl groups unsubstituted or wherein the methyl group is substituted with 1 to 3 fluoro atoms;

R$_{14}$ is hydrogen or R$_7$; or when R$_8$ and R$_{14}$ are as NR$_8$R$_{14}$ they may together with the nitrogen form a 5 to 7 membered ring comprised only of carbon atoms or carbon atoms and at least one heteroatom selected from O, N, or S; provided that:

(f) R$_7$ is not C$_{1-4}$ alkyl unsubstituted or substituted by one to three fluorines; or or the pharmaceutically acceptable salts thereof.

2. A compound according to claim 1 wherein R$_1$ is —CH$_2$-cyclopropyl, -cyclopentyl, -3-hydroxycyclopentyl, methyl or CF$_2$H; X is YR$_2$; Y is oxygen; X$_2$ is oxygen; X$_3$ is hydrogen; R$_2$ is CF$_2$H or methyl, W is ethynyl or 1,3-butadiynyl, R$_3$ is a substituted or unsubstituted pyrimidinyl ring, X is YR$_2$, and Z is O, NR$_7$.

3. A compound according to claim 2 which is 4-(3-cyclopentyloxy-4-methoxyphenyl)-4-(2-methylsulfonylpyrimidin-4-ylethynyl) cyclohexan-1-one, 4-(2-aminopyrimidin-4-ylethynyl)-4-(3-cyclopentyloxy-4-methoxyphenyl)cyclohexan-1-one, or 4-(2-acetamidopyrimidin-5-ylethynyl)-4-(3-cyclopentyloxy-4-methoxyphenyl)cyclohexan-1-one.

4. A compound according to claims 1 wherein R$_1$ is —CH$_2$-cyclopropyl, -cyclopentyl, -3-hydroxycyclopentyl, methyl or CF$_2$H; X is YR$_2$; Y is oxygen; X$_2$ is oxygen; X$_3$ is hydrogen; R$_2$ is CF$_2$H or methyl, W is ethynyl or 1,3-butadiynyl, R$_3$ R$_3$ is R$_7$ where R$_7$ is an unsubstituted or substituted aryl or heteroaryl ring, X is YR$_2$, and Z is O.

5. A compound according to claim 4 which is 4-(3-cyclopentyloxy-4-methoxyphenyl)-4-(4-aminophenylethynyl)cyclohexan-1-one, 4-(3-cyclopentyloxy-4-methoxyphenyl)-4-(4-acetamidophenylethynyl)cyclohexan-1-one, 4-(3-cyclopentyloxy-4-methoxyphenyl)-4-(3-acetamidophenylethynyl)cyclohexan-1-one, 4-(3-cyclopentyloxy-4-methoxyphenyl)-4-(3-carbomethoxyphenylethynyl)cyclohexan-1-one, 4-(3-cyclopentyloxy-4-methoxyphenyl)-4-(3-carboxyphenylethynyl)cyclohexane-1-one, 4-(3-cyclopentyloxy-4-methoxyphenyl)-4-(3-aninophenylethynyl)cyclohexan-1-one 4-(3-cyclopentyloxy-4-methoxyphenyl)-4-(4-pyridylethynyl)cyclohexan-1-one, 4-(3-cyclopentyloxy-4-methoxyphenyl)-4-{[4-(2-hydroxyethan-1-oxy)phenyl]ethynyl}cyclohexan-1-one, 4-(3-cyclopentyloxy-4-methoxyphenyl)-4-(3-pyridylethynyl)cyclohexan-1-one, 4-(3-cyclopentyloxy-4-methoxyphenyl)-4-(2-[4-(2-hydroxyethan-1-oxy)phenyl]ethynyl)cyclohexan-1-one, 4-(4-carbomethoxyphenylethynyl)-4-(3-cyclopentyloxy-4-methoxyphenyl)cyclohexan-1-one, 4-(4-carboxyphenylethynyl)-4-(3-cyclopentyloxy-4-methoxyphenyl)cyclohexan-1-one, 4-(3-cyclopentyloxy-4-methoxyphenyl)-4-(2-[4-(1-piperidinocarbonylmethoxy)phenyl]ethynyl) Cyclohexan-1-one, 4-(2-[4-carboxymethyloxyphenyl] ethynyl)-4-(3-cyclopentyloxy-4-methoxyphenyl) cyclohexan-1-one, 4-(2-[4-carbomethoxymethyloxyphenyl]ethynyl)-4-(3-cyclopentyloxy-4-methoxyphenyl)cyclohexan-1-one, 4-(2-carbomethoxyphenylethynyl)-4-(3-cyclopentyloxy-4-methoxyphenyl)cyclohexan-1-one, 4-(3-cyclopentyloxy-4-methoxyphenyl)-4-(2-[3,5-dicarbomethoxyphenyl]ethynyl)cyclohexan-1-one, 4-(2-[4-chlorophenyl]ethynyl)-4-(3-cyclopentyloxy-4-methoxyphenyl)cyclohexan-1-one, 4-(2-carbomethoxythien-5-ylethynyl)-4-(3-cyclopentyloxy-4-methoxyphenyl)cyclohexan-1-one, 4-(2-[3-cyanophenyl]ethynyl)-4-(3-cyclopentyloxy-4-methoxyphenyl)cyclohexan-1-one, 4-(3-cyclopentyloxy-4-methoxyphenyl)-4-(2-[4-hydroxyphenyl]ethynyl)cyclohexan-1-one, 4-(3-cyclopentyloxy-4-methoxyphenyl)-4-(2[E]-(3-cyanophenyl)ethenyl)cyclohexan-1-one, 4-(3-cyclopentyloxy-4-methoxyphenyl)-4-(2-[3,5-dicyanophenyl]ethynyl)cyclohexan-1-one, 4-(2-carboxythien-5-ylethynyl)-4-(3-cyclopentyloxy-4-methoxyphenyl)cyclohexan-1-one, sodium salt, 4-(2-cyanothien-5-ylethynyl)-4-(3-cyclopentyloxy-4-methoxyphenyl)cyclohexan-1-one, 4-(3-cyclopentyloxy-4-methoxyphenyl)-4-[5-(5-methyl-[1,2,4]oxadiazol-2-yl)thien-2-ylethynyl]cyclohexan-1-one, 4-(3-cyclopentyloxy-4-methoxyphenyl)-4-(2-[3-(5-methyl-[1,2,4]oxadiazol-3-yl)phenyl]ethynyl) cyclohexan-1-one, 4-(3-cyclopentyloxy-4-methoxyphenyl)-4-(2-[3-(3-methyl-[1,2,4]oxadiazol-5-yl)phenyl]ethynyl)cyclohexan-1-one, 4-(3-cyclopentyloxy-4-methoxyphenyl)-4-[4-(5-methyl-[1,2,4]oxadiazol-2-yl)thien-2-ylethynyl]cyclohexan-1-one, 4-(3-Cyclopentyloxy-4-methoxyphenyl)-4-(2-[3-(5-methyl-[1,3,4]oxadiazol-2-yl)phenyl]ethynyl) cyclohexan-1-one, 4-(2-Carbomethoxythien-4-ylethynyl)-4-(3-cyclopentyloxy-4-methoxyphenyl) cyclohexan-1-one, SB 4-(2-Carboxythien-4-ylethynyl)-4-(3-cyclopentyloxy-4-methoxyphenyl)cyclohexan-1-one, S 4-(2-cyanothien-4-ylethynyl)-4-(3-cyclopentyloxy-4-methoxyphenyl)cyclohexan-1-one -(3-cyclopentyloxy-4-methoxyphenyl)-4-(2-[3-(3-methyl [1,2,4]oxadiazol-5-yl)phenyl]ethynyl)cyclohexan-1-one, SB 4-(3-cyclopentyloxy-4-methoxyphenyl)-4-[2-(5-methyl-[1,2,4]oxadiazol-2-yl)thien-4-ylethynyl]cyclohexan-1-one, 4-(4-carbomethoxythien-2-ylethynyl)-4-(3-cyclopentyloxy-4-methoxyphenyl)cyclohexan-1-one, 4-(4-carboxythien-2-ylethynyl)-4-(3-cyclopentyloxy-4-methoxyphenyl)cyclohexan-1-one, 4-(3-cyclopentyloxy-4-methoxyphenyl)-4-(2-[3-(5-methyl-[1,3,4]thiadiazol-2-yl)phenyl]ethynyl) cyclohexan-1-one, 4-(3-cyclopentyloxy-4-methoxyphenyl)-4-(1-methylimidazol-2-ylethynyl) cyclohexan-1-one, 4-(3-cyclopentyloxy-4-methoxyphenyl)-4-(imidazol-2-ylethynyl)cyclohexan-1-one, hydrochloride salt, 4-(2-acetamidopyrimidin-5-ylethynyl)-4-(3-cyclopentyloxy-4-methoxyphenyl)cyclohexan-1-one, 4-(3-cyclopentyloxy-4-methoxyphenyl)-4-(2-[3-(5-methyl[1,3,4]oxadiazol-2-yl)phenyl]ethynyl) cyclohexan-1-one, or 4-(3-cyclopentyloxy-4-methoxyphenyl)-4-(2-[3-(5-methyl[1,3,4]thiadiazol-2-yl)phenyl]ethynylcyclohexan-1-one.

6. A compound of Formula II

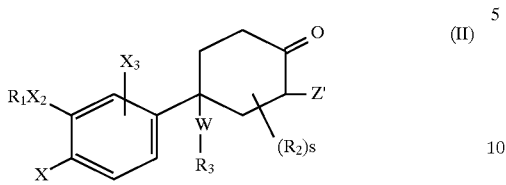

wherein:
R₁ is -(CR₄R₅)ₙC(O)O(CR₄R₅)ₘR₆, —(CR₄R₅)ₙC(O)NR₄(CR₄R₅)ₘR₆, —(CR₄R₅)ₙO(CR₄R₅)ₘR₆, or —(CR₄R₅)ᵣR₆ wherein the alkyl moieties may be unsubstituted or substituted with one or more fluorines;
m is 0 to 2;
n is 0 to 4;
r is 0 to 6;
R₄ and R₅ are independently selected hydrogen or C₁₋₂ alkyl;
R₆ is hydrogen, methyl, hydroxyl, aryl, halo substituted aryl, aryloxyC₁₋₃ alkyl, halo substituted aryloxyC₁₋₃ alkyl, indanyl, indenyl, C₇₋₁₁ polycycloalkyl, tetrahydrofuranyl, furanyl, tetrahydropyranyl, pyranyl, tetrahydrothienyl, thienyl, tetrahydrothiopyranyl, thiopyranyl, C₃₋₆ cycloalkyl, or a C₄₋₆ cycloalkyl containing one or two unsaturated bonds, wherein the cycloalkyl and heterocyclic moieties is unsubstituted or substituted by 1 to 3 methyl groups, an ethyl group, or an hydroxyl group;
provided that:
a) when R₆ is hydroxyl, then m is 2; or
b) when R₆ is hydroxyl, then r is 2 to 6; or
c) when R₆ is 2-tetrahydropyranyl, 2-tetrahydrothiopyranyl, 2-tetrahydrofuranyl, or 2-tetrahydrothienyl, then m is 1 or 2; or
d) when R₆ is 2-tetrahydropyranyl, 2-tetrahydrothiopyranyl, 2-tetrahydrofuranyl, or 2-tetrahydrothienyl, then r is 1 to 6;
e) when n is 1 and m is 0, then R₆ is other than H in —(CR₄R₅)ₙO(CR₄R₅)ₘR₆;
X is YR₂, fluorine, NR₄R₅, or formyl amine;
Y is O or S(O)ₘ';
m' is 0, 1, or 2;
X₂ is O or NR₈;
X₃ is hydrogen or X;
R₂ is independently selected from —CH₃ or —CH₂CH₃ unsubstituted or substituted by 1 or more fluorines;
s is 0 to 4;
R₃ is COOR₁₄, C(O)NR₄R₁₄ or R₇;
W is alkyl of 2 to 6 carbons, alkenyl of 2 to 6 carbon atoms or alkynyl of 2 to 6 carbon atoms;
Z' is C(Y')R₁₄, C(O)OR₁₄, C(Y')NR₁₀R₁₄, C(NR₁₀)NR₁₀R₁₄, CN, C(NOR₈)R₁₄, C(O)NR₈NR₈C(O)R₈, C(O)NR₈NR₁₀R₁₄, C(NOR₁₄)R₈, C(NR₈)NR₁₀R₁₄, C(NR₁₄)NR₈R₈ C(NCN)NR₁₀R₁₄, C(NCN)SR₉, (2-, 4- or 5-imidazolyl), (3-, 4- or 5-pyrazolyl), (4- or 5-triazolyl[1,2,3]), (3- or 5-triazolyl[1,2,4]), (5-tetrazolyl), (2-, 4- or 5-oxazolyl), (3-, 4- or 5-isoxazo, (3- or 5-oxadiazolyl[1,2,4]), (2-oxadiazolyl[1,3,4]), (2-thiadiazolyl[1,3,4]), (2-, 4-, or 5-thiazolyl), (2-, 4-, or 5-oxazolidinyl), (2-, 4-, or 5-thiazolidinyl), or (2-, 4-, or 5-imidazolidinyl); wherein all of the heterocylic ring systems may be optionally substituted one or more times by R₁₄;
Y' is O or S;
R₇ is —(CR₄R₅)qR₁₂ or C₁₋₆ alkyl wherein the R₁₂ or C₁₋₆ alkyl group is unsubstituted or substituted one or more times by methyl or ethyl unsubstituted or substituted by 1–3 fluorines, —F, —Br, —Cl, —NO₂, —NR₁₀R₁₁, —C(O)R₈, —CO₂R₈, —O(CH₂)₂₋₄OR₈, —O(CH₂)qR₈, —CN, —C(O)NR₁₀R₁₁, —O(CH₂)qC(O)NR₁₀R₁₁, —O(CH₂)qC(O)R₉, —NR₁₀C(O)NR₁₀R₁₁, —NR₁₀C(O)R₁₁, —NR₁₀C(O)OR₉, —NR₁₀C(O)R₁₃, —C(NR₁₀)NR₁₀R₁₁, —C(NCN)NR₁₀R₁₁, —C(NCN)SR₉, —NR₁₀C(NCN)SR₉, —NR₁₀C(NCN)NR₁₀R₁₁, —NR₁₀S(O)₂R₉, —S(O)ₘ'R₉, —NR₁₀C(O)C(O)NR₁₀R₁₁, —NR₁₀C(O)C(O)R₁₀, or R₁₃;
q is 0, 1, or 2;
R₁₂ is R₁₃, (CH₂)q, C₃–C₇ cycloalkyl, (2-, 3- or 4-pyridyl), pyrimidyl, pyrazolyl, (1- or 2-imidazolyl), pyrrolyl, piperazinyl, piperidinyl, morpholinyl, furanyl, (2- or 3-thienyl), quinolinyl, naphthyl, or phenyl;
R₈ is independently selected from hydrogen or R₉;
R₉ is C₁₋₄ alkyl unsubstituted or substituted by one to three fluorines;
R₁₀ is OR₈ or R₁₁;
R₁₁ is hydrogen, or C₁₋₄ alkyl unsubstituted or substituted by one to three fluorines; or when R₁₀ and R₁₁ are as NR₁₀R₁₁ they may together with the nitrogen form a 5 to 7 membered ring comprised only of carbon atoms or carbon atoms and at least one heteroatom selected from O, N, or S;
R₁₃ is a substituted or unsubstituted heteroaryl group selected from the group consisting of oxazolidinyl, oxazolyl, thiazolyl, pyrazolyl, triazolyl, tetrazolyl, imidazolyl, imidazolidinyl, thiazolidinyl, isoxazolyl, oxadiazolyl, and thiadiazolyl, and where R₁₃ is substituted on R₁₂ or R₁₃ the rings are connected through a carbon atom and each second R₁₃ ring may be unsubstituted or substituted by one or two C₁₋₂ alkyl groups unsubstituted or substituted on the methyl with 1 to 3 fluoro atoms;
R₁₄ is hydrogen or R₇; or when R₈ and R₁₄ are as NR₈R₁₄ they may together with the nitrogen form a 5 to 7 membered ring comprised only of carbon atoms or carbon atoms and at least one heteroatoms selected from O, N, or S;
provided that:
(f) R₇ is not C₁₋₄ alkyl unsubstituted or substituted by one to three fluorines;
or the pharmaceutically acceptable salts thereof.

7. A compound according to claim 6 R₁ is —CH₂-cyclopropyl, -cyclopentyl, -3-hydroxycyclopentyl, methyl or $CF_2H$; X is $YR_2$; Y is oxygen; $X_2$ is oxygen; $X_3$ is hydrogen; $R_2$ is $CF_2H$ or methyl, W is ethynyl or 1,3-butadiynyl, $R_3$ $R_3$ is $R_7$ where $R_7$ is an unsubstituted or substituted aryl or heteroaryl ring, X is $YR_2$, Z is O, and Z' is $COOR_{14}$.

8. A compound according to claim 7 wherein W is 1,3-butadiynyl and $R_3$ is unsubstituted or substituted pyrimidin-5-yl.

9. A pharmaceutically composition comprising a compound according to claim 1 and a pharmaceutically acceptable excipient.

10. A method for treating asthma which comprises administering to a mammal, including humans, in need thereof, an effective amount of a compound according to claim 1.

* * * * *